(12) United States Patent
Ramsing et al.

(10) Patent No.: US 11,649,425 B2
(45) Date of Patent: May 16, 2023

(54) LID FOR CULTURE DISH

(71) Applicant: Vitrolife A/S, Viby (DK)

(72) Inventors: Niels B. Ramsing, Egå (DK); Troels Kofoed Mejer, Skødstrup (DK); Kim Lund Madsen, Viby J (DK); Lisbeth Kongsbak Lyngberg, Braband (DK); Jonas Lerche Hansen, Hinnerup (DK)

(73) Assignee: VITROLIFE A/S, Viby (DK)

( * ) Notice: Subject to any disclaimer, the term of this patent is extended or adjusted under 35 U.S.C. 154(b) by 159 days.

(21) Appl. No.: 16/619,080

(22) PCT Filed: Jun. 5, 2018

(86) PCT No.: PCT/EP2018/064753
§ 371 (c)(1),
(2) Date: Dec. 3, 2019

(87) PCT Pub. No.: WO2018/224492
PCT Pub. Date: Dec. 13, 2018

(65) Prior Publication Data
US 2020/0095529 A1    Mar. 26, 2020

(30) Foreign Application Priority Data
Jun. 8, 2017    (GB) ...................................... 1709140

(51) Int. Cl.
*C12M 1/00*     (2006.01)
*C12M 1/32*     (2006.01)
*C12M 1/04*     (2006.01)

(52) U.S. Cl.
CPC ............ *C12M 23/38* (2013.01); *C12M 23/12* (2013.01); *C12M 23/24* (2013.01)

(58) Field of Classification Search
CPC ....... C12M 23/38; C12M 23/12; C12M 23/24
(Continued)

(56) References Cited

U.S. PATENT DOCUMENTS 6,156,566 A * 12/2000 Bryant ................... C12M 23/10
                                                                435/305.3
6,521,451 B2   2/2003 Potter
(Continued)

FOREIGN PATENT DOCUMENTS

CN        102015997 A    4/2011
CN        205669023 U   11/2016
(Continued)

OTHER PUBLICATIONS

S.J. Metz, Water Vapor and Gas Transport Through Polymeric Membranes (Year: 2003).*
(Continued)

*Primary Examiner* — Michael L Hobbs
*Assistant Examiner* — Lenora A Abel
(74) *Attorney, Agent, or Firm* — Honigman LLP

(57) ABSTRACT

An apparatus comprising a culture dish and a removable lid, wherein the culture dish comprises a main body having a side wall defining a reservoir region for receiving a quantity of liquid media, and the removable lid is arranged to cover the reservoir region during normal use, wherein the lid comprises a gas permeable material and includes an engagement portion formed of a resilient material adapted to cooperatively engage with the side wall of the main body of the culture dish so as to compress a part of the engagement portion of the removable lid against the side wall to form a vapour-tight seal for the reservoir region when the removable lid is coupled to the culture dish. The lid fitted to the culture dish enables a substantial portion of the culturing (Continued)

media to remain in the environment enclosed between the reservoir and the lid without use of a cover media to limit evaporation while allowing gaseous exchange therethrough.

22 Claims, 8 Drawing Sheets

(58) Field of Classification Search
USPC ...................................................... 435/288.4
See application file for complete search history.

(56) References Cited

U.S. PATENT DOCUMENTS

| | | | |
|---|---|---|---|
| 7,373,968 B2* | 5/2008 | Oldenburg | C25D 17/06 165/200 |
| 7,842,246 B2* | 11/2010 | Wohlstadter | B01L 9/50 422/401 |
| 8,828,337 B2 | 9/2014 | Kensy et al. | |
| 2001/0024821 A1 | 9/2001 | Potter | |
| 2010/0055790 A1* | 3/2010 | Simon | C12M 23/12 435/383 |
| 2010/0248995 A1* | 9/2010 | Kensy | C12M 23/12 506/39 |
| 2013/0084622 A1* | 4/2013 | Ram | C12M 29/18 435/252.8 |
| 2013/0210123 A1 | 8/2013 | Malcolm et al. | |

FOREIGN PATENT DOCUMENTS

| | | |
|---|---|---|
| EP | 0866122 | 9/1998 |
| EP | 1864716 | 12/2007 |
| FR | 2486915 | 1/1982 |
| JP | 05260951 A | 10/1993 |
| JP | 2005312317 | 11/2005 |
| WO | 2009136907 A1 | 11/2009 |
| WO | 2012/095678 | 7/2012 |
| WO | 2015/169499 | 11/2015 |
| WO | WO-2015169499 A1 * | 11/2015 ............ C12M 41/36 |

OTHER PUBLICATIONS

International Search Report and Written Opinion for PCT/EP2018/064753 dated Sep. 21, 2018.
Office Action mailed for GB1709140.6 dated Mar. 16, 2018.
Journal of Biosciences, vol. 34, No. 1, epub Feb. 2009, A Blau, et al., "Replica-moulded polydimethylsiloxan culture vessel lids attenuate osmotic drift in long-term cell cultures", pp. 59-69 and online supplementary information.
International Preliminary Report on Patentability for PCT/EP2018/064753 dated Dec. 19, 2019.
Office Action issued in CN 201880048308.X dated Feb. 28, 2023.

* cited by examiner

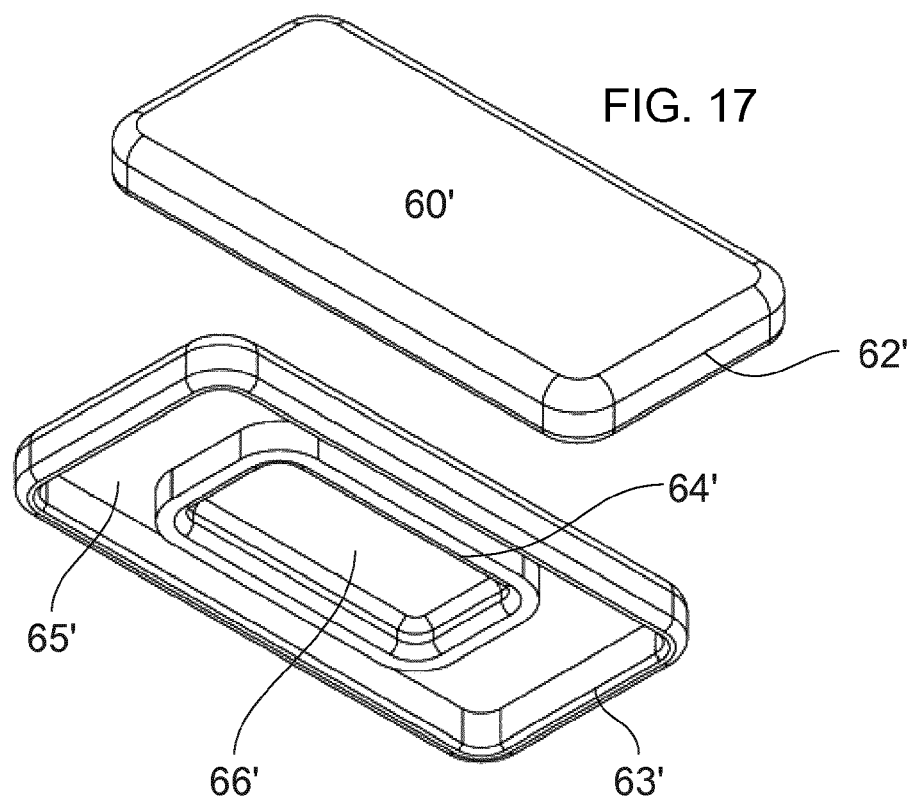
FIG. 17
FIG. 18
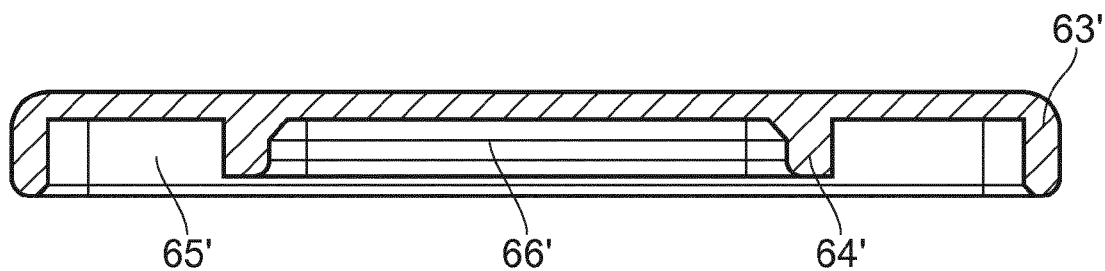
FIG. 19

LID FOR CULTURE DISH

CLAIM OF PRIORITY

This application claims priority under 35 USC 371 to International Application No. PCT/EP2018/064753, filed on Jun. 5, 2018, which claims priority to GB Application No. 1709140.6, filed Jun. 8, 2017, each of which is incorporated by reference in its entirety.

BACKGROUND OF THE INVENTION

The present invention relates to culture dishes. More particularly, certain embodiments relate to culture dishes for incubating embryos.

Infertility affects more than 80 million people worldwide. It is estimated that 10% of all couples experience primary or secondary infertility. In vitro fertilization (IVF) is an elective medical treatment that may provide a couple who has been otherwise unable to conceive a chance to establish a pregnancy. It is a process in which eggs (oocytes) are taken from a woman's ovaries and then fertilized with sperm in the laboratory. The embryos created in this process are then placed into the uterus for potential implantation. In between fertilization (insemination) and transfer the embryos are typically stored in an incubation chamber of an incubator for 2-6 days during which time they may be regularly monitored, for example through imaging, to assess their development. Conditions within the incubator, such as temperature and atmospheric composition, are controlled, generally with a view to emulating the conditions in the oviduct and uterus.

Embryos for incubation are typically placed in culture dishes, which may then be stored in the incubator. Culture dishes may also be referred to as slides, carriers or trays.

One well-known apparatus for incubating embryos, and which also provides for time-lapse embryo imaging to assess embryo development, is the EmbryoScope® device with its associated EmbryoViewer® software developed by, and available from, Vitrolife A/S (Aarhus, Denmark). The EmbryoScope® D apparatus has the ability to incubate embryos in six removable culture dishes called slides supported by a slide carrier. Each slide (dish) comprises a 3×4 array of receptacles and so is able to hold up to 12 embryos. For the EmbryoScope®+apparatus, there are 15 removable culture dishes and a 4×4 array of receptacles for holding up to 16 embryos in each culture dish. In use, each embryo to be incubated is placed in a separate receptacle in its own media droplet separate from the others or in a droplet shared with other embryos, and in both cases covered with a larger volume of mineral oil to prevent evaporation during incubation. The EmbryoScope® apparatus has a built-in microscope and translation stage to allow the embryos to be sequentially imaged at different stages throughout their incubation.

FIG. 1 is a schematic perspective view of an embryo dish/slide 2 of the kind typically used in the EmbryoScope® D device. The dish 2 has overall dimensions of around 7.5 cm (length)×2.5 cm (width)×1.5 cm (height) and is formed as a single injection moulding of a plastics material, for example a transparent polyester material. The slide 2 comprises a main body 4, a handle 6 for holding the dish, and a labelling area 8 on which a label may be stuck with information relating to the embryos on the slide (e.g. patient ID and incubation protocol information). A 3×4 array of receptacles (wells) 10 for receiving individual embryos for culturing are provided within a recess 12 in the main body 4. The recess 12 is defined by a recess floor 14, in which the receptacles 10 are provided and recess walls 16. The recess has dimensions of around 3.5 cm (length)×2.0 cm (width)× 0.8 cm (depth). The normal orientation for the slide 2 during use is with the recess floor 14 horizontal and the recess walls 16 vertical. The receptacles 10 have a diameter of around 4 mm at the recess floor and have vertical walls extending downwards from the recess floor for around 2.5 mm before tapering to a smaller sub-millimetre (e.g. around 0.3 mm diameter) well 18 in which an embryo is located for culturing. Within the recess 12 there is also provided four (two at each end) flush reservoirs 20. These may be used to store liquids, for example washing media, used while the embryos are prepared for culturing/incubation in accordance with whichever protocols are being followed. In normal use individual embryos are located in respective ones of the sub-millimetre wells 18 at the bottom of the receptacles 10. The number of wells 10 containing an embryo on any given slide will depend on the number of embryos to be incubated using that slide. It is common to avoid mixing embryos from different patients on the same slide, and so if there are not enough embryos from a patient to fill a complete slide, the remaining receptacles for the slide will generally remain unused. Each receptacle 10 containing an embryo is filled (to a level below the recess floor 14) with a water-based culturing media for the embryo. The recess 12 is then at least partially filled with an oil layer that overlays the culturing (growth) media in the receptacles 10. The oil layer provides a barrier to help reduce evaporation of the culturing media in which the embryos are located. The oil overlay layer is also present to help prevent or substantially reduce contamination by acting as a hydrophobic barrier to vira, bacteria, fungi and potentially toxic volatile organic compounds (VOC). The oil overlay is mandatory to prevent evaporation, which induce osmotic stress, when incubating in a dry incubator but may be omitted when incubating in a humidified environment. However, humidified incubators are more readily contaminated by fungi and bacteria that may proliferate in such settings, and as a result many IVF labs thus prefer to incubate embryos in dry incubators using an oil overlay. The EmbryoScope® is an example of a dry incubator. The oil layer may unfortunately also be an unwanted source of toxins, so high purity and IVF tested oils are routinely purchased from specialized suppliers and used for embryo culturing.

The geometry and dimensions of the dish 2 represented in FIG. 1 are adapted to match those of the specific apparatus in which the embryos are to be incubated using the slide. However, broadly corresponding designs of culture dish/ embryo slide may be used for other incubator/culturing apparatus.

More details on the characteristics of known culture dishes suitable for use in embryo incubation can be found, for example, in WO 09/003487 (Unisense Fertilitech A/S) [1], WO 01/002539 (The Danish Institute of Agricultural Sciences) [2], and WO 2015/169499 (Unisense Fertilitech A/S) [3].

Although not shown in FIG. 1, the slide 2 has a separate lid that is placed over the main body 4 containing the recess 12. The separate lid is generally formed from a transparent polymer material and has a cuboidal shape comprising a recessed portion. The recessed portion is sized to receive the main body 4 of the culture dish and is loosely fit over the main body 4 after embryos have been located in the wells 18 and the culturing media and oil placed in the receptacles 10 and recess 12 respectively. Oxygen and carbon dioxide exchange between the environment within the slide 2 (i.e., within recess 12) and the environment outside the slide 2 can occur through the loose fitting of the lid and the main body 4, e.g., through spaces/gaps between the main body 4 and lid. This gaseous exchange is necessary for embryo development.

Two gases are required for embryo development: oxygen and carbon dioxide and most incubators provide a controlled mixture of these two gasses and nitrogen (e.g. 6% $CO_2$, 5% $O_2$ and 89% $N_2$) and are thus often referred to as tri-gas incubators, though it should be noted that the nitrogen is not consumed by the growing embryo. Embryos consume oxygen during their development. However, the amounts consumed are minuscule, and are readily replenished by molecular diffusion from the large amounts of oxygen gas contained inside the culture dish. Still there are strong indications in the scientific literature that the oxygen tension in the oviduct (where embryos normally reside) is reduced from atmospheric levels of oxygen (approximately 20% $O_2$), and that incubation of IVF embryos at reduced oxygen concentration is beneficial for embryo development. Many IVF clinics thus prefer to reduce the oxygen concentration from atmospheric to around 5% $O_2$ within the incubators used to culture human embryos in IVF. An efficient gaseous exchange in the culture dish is thus necessary to ensure that the embryo is exposed to the correct reduced oxygen concentration within the incubator.

Carbon dioxide is not used (but produced in tiny amounts) by the embryos. However, most commercial culturing media use bicarbonate based buffering systems, and maintaining the correct pH (around 7.2 to 7.4) in the culturing/growth media is essential for embryo development and survival. In most media formulations this corresponds to a $CO_2$ concentration of 5% to 6% (at sea level). An efficient gaseous exchange in the culture dish is thus absolutely necessary to ensure that the pH of the culturing media is in the correct range, which is controlled by exposing the culturing media to the correct carbon dioxide concentration within the incubator. As culturing media formulations and even different batches of culturing media from the same supplier may differ, it is important for the IVF clinic to measure and validate the pH of a media sample incubated in the incubator for any given $CO_2$ concentration setting. The common routine procedure to validate pH involves placing a culturing media sample in a culture dish without embryos inside the incubator to equilibrate for at least 24 hours, before removing the sample and quickly measuring the pH of the culturing media. In case of dry incubators, the culturing media sample has to be covered with an oil layer to prevent evaporation. Evaporation will change the pH of the remaining culturing media due to changes in osmolality and possibly evaporative cooling. However, a covering oil layer may interfere with pH measurements using conventional pH electrodes and may even damage the electrodes and compromise the measurements. The oil layer also takes up space in the culture dish, and the amount of culturing media ideally required for pH measurements with conventional pH electrodes often exceeds the available amount when leaving room for oil cover.

While the loose fitting, separate lid is necessary for efficient gaseous exchange, it does not provide any protection against accidental mishandling such as spilling or dropping slides, and contamination of incubators and laboratory space with pathogens from patients suffering from known diseases such as HIV or hepatitis. Great care is taken to handle all culture dishes safely, but accidents do happen, and may cause spilling of media containing embryos, which cannot be recovered. This will reduce the chance of a successful outcome if some embryos are lost, and may require a new treatment. A further risk is potential contamination by pathogens or virus if media containing embryos from a patient with a disease is treated in the clinic. To reduce this risk most clinics require that their patients have diagnostic tests for common viral infections such as HIV and hepatitis, and patients carrying such diseases are normally treated with special procedures and placed in dedicated incubators for embryos only from such patients. These procedures are consequently more labour-intensive and expensive as they require additional equipment. Furthermore there is always a possibility that a diagnostic test has failed to detect a potential infection.

While culture dishes of the kind represented in FIG. 1 and associated separate lids have been found to be successful in facilitating embryo incubation, and in particular in the context of time-lapse imaging systems, the present inventors have nonetheless recognised there are still some aspects of the design which could be improved.

SUMMARY OF THE INVENTION

According to a first aspect of the invention there is provided an apparatus comprising a culture dish and a removable lid, wherein the culture dish comprises a main body having a side wall defining a reservoir region for receiving a quantity of liquid media, and the removable lid is arranged to cover the reservoir region during normal use, wherein the lid comprises a gas permeable material and includes an engagement portion formed of a resilient material adapted to cooperatively engage with the side wall of the main body of the culture dish so as to compress a part of the engagement portion of the removable lid against the side wall to form a vapour-tight seal for the reservoir region when the removable lid is coupled to the culture dish.

According to a second aspect of the invention there is provided a removable lid for use with a culture dish, the culture dish having a main body comprising side wall defining a reservoir region for receiving a quantity of liquid media, wherein the removable lid is arranged to cover the reservoir region during normal use, wherein the lid comprises a gas permeable material and includes an engagement portion formed of a resilient material adapted to cooperatively engage with the side wall of the main body of the culture dish so as to compress a part of the engagement portion of the removable lid against the side wall to form a vapour-tight seal for the reservoir region when the removable lid is coupled to the culture dish.

According to a third aspect of the invention there is provided a culture dish having a main body comprising a side wall defining a reservoir region for receiving objects to be cultured and a quantity of culturing media, the culture dish configured to receive a removable lid according to the second aspect.

According to a fourth aspect of the invention there is provided a mould for forming the removable lid according to the second aspect.

According to a fifth aspect of the invention there is provided a method of culturing at least one object, the method comprising: providing a culture dish having a side wall defining a reservoir region; placing one or more objects to be cultured and a quantity of liquid media within the reservoir region of the culture dish; applying a removable lid to cover the reservoir region, wherein the removable lid comprises a gas permeable material and includes an engagement portion formed of a resilient material adapted to cooperatively engage with the side wall of the main body of the culture dish so as to compress a part of the engagement portion of the removable lid against the side wall to form a vapour-tight seal for the reservoir region when the removable lid is coupled to the culture dish; and allowing the one or more objects to culture.

According to a sixth aspect of the invention there is provided a method of determining culture conditions such as pH within a culture dish, the method including: providing a culture dish having a side wall defining a reservoir region; placing a quantity of liquid media within the reservoir region of the culture dish; applying a removable lid to cover the reservoir, wherein the removable lid comprises a gas permeable material and includes an engagement portion formed of a resilient material adapted to cooperatively engage with the side wall of the main body of the culture dish so as to compress a part of the engagement portion of the removable lid against the side wall to form a vapour-tight seal for the reservoir region when the removable lid is coupled to the culture dish; placing the culture dish in an incubating apparatus and allowing the dish to equilibrate with the environment within the incubating apparatus; and performing measurements such as pH measurements on the liquid media within the reservoir region after equilibration.

It will be appreciated that features and aspects of the invention described above in relation to the first and other aspects of the invention are equally applicable to, and may be combined with, embodiments of the invention according to other aspects of the invention as appropriate, and not just in the specific combinations described above.

BRIEF DESCRIPTION OF THE DRAWINGS

The invention is now described by way of example only with reference to the following drawings in which:

FIGS. 17 to 19 schematically represent different views of a resilient lid suitable for use with the culture dish of FIG. 1;

DETAILED DESCRIPTION

Figure 1:
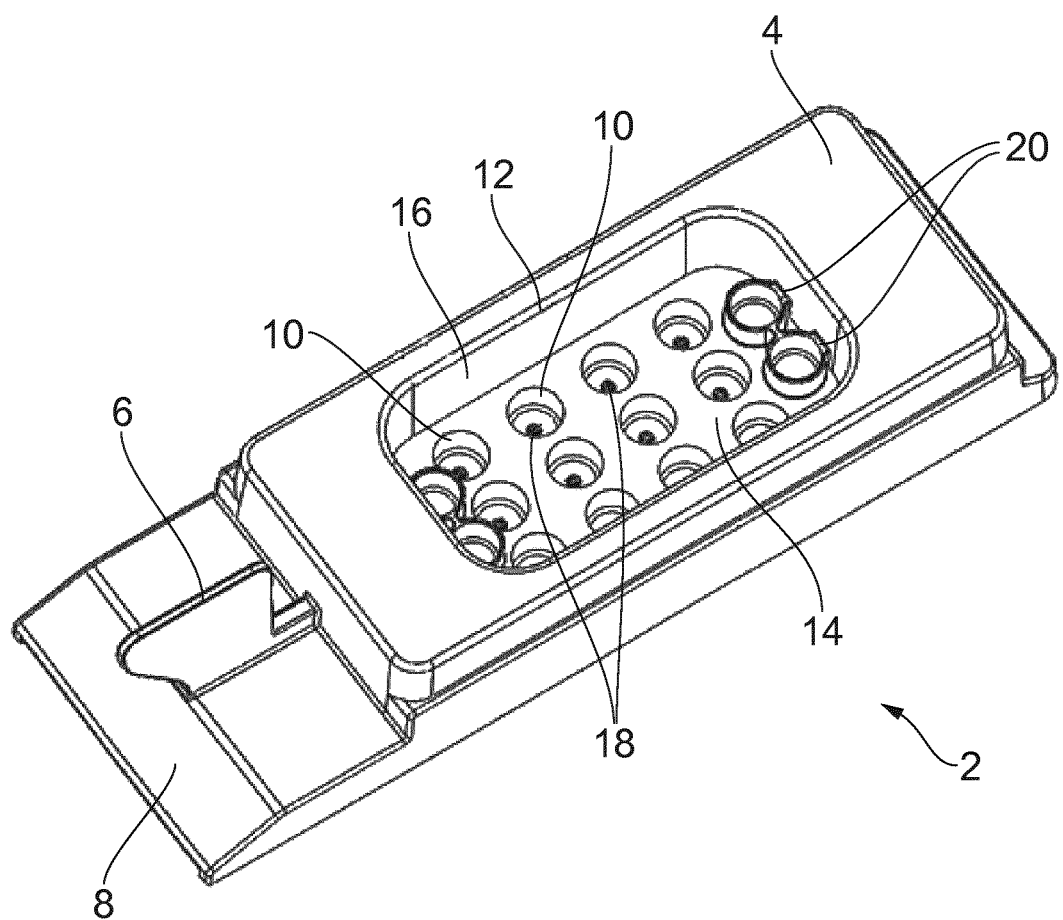
FIG. 1 schematically represents in perspective view a known culture dish to be used for incubating embryos.

Aspects and features of certain examples and embodiments of the present invention are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with conventional techniques for implementing such aspects and features.

Unless the context demands otherwise, the terms used herein should be interpreted in accordance with their meanings as commonly understood by one of ordinary skill in the art to which this disclosure belongs.

Embryos are typically incubated for a period of up to 3 to 6 days following fertilisation. In some respects the term "embryo" may sometimes be used to refer to a fertilised oocyte (egg) after implantation in the uterus until 8 weeks after fertilization, at which stage it become a fetus. In accordance with this terminology the fertilized oocyte may be sometimes called a pre-embryo or zygote until implantation occurs. However, for convenience the term "embryo" may sometimes also be used to encompass the zygote stage and subsequent stages prior to implantation, and this approach will generally be followed herein. That is to say, the term "embryo" is used herein in a broad sense to cover all developmental stages from fertilization of an oocyte through cleavage stages, morula, blastocyst stages, hatching and implantation. Accordingly, the term embryo may be used herein to denote each of the stages: fertilized oocyte, 2-cell, 4-cell, 8-cell, 16-cell, compaction, morula, blastocyst, expanded blastocyst and hatched blastocyst, as well as all stages in between (e.g. 3-cell or 5-cell) stages. Thus, the terms embryo and zygote may be used herein interchangeably, for example. An embryo that is incubated using a culture dish in accordance with embodiments of the invention such as described herein may be previously frozen, e.g. embryos cryopreserved immediately after fertilization (e.g. at the 1-cell stage) and then thawed. Alternatively, they may be freshly prepared, e.g. embryos that are freshly prepared from oocytes by IVF or ICSI techniques for example.

An embryo is approximately spherical and is composed of one or more cells (blastomeres) surrounded by a gelatine-like shell, the acellular matrix known as the zona pellucida. The zona pellucida performs a variety of functions until the embryo hatches, and is a good landmark for embryo evaluation. The zona pellucida is spherical and translucent, and should be clearly distinguishable from cellular debris.

As noted above, embryos are sometimes stored/held in a culture dish, for example during in vitro fertilization (IVF) procedures. In this context a culture dish may also be referred to as an (embryo) slide, (embryo) carrier or (embryo) tray. As also noted above, a culture dish for use in embryology will typically comprise a plurality of wells for receiving embryos to be cultured. Embryos in respective wells are submerged in a water-based growth media (culturing media) which is overlaid by a layer of oil.

Culture dishes and associated lids of the kind described in relation to FIG. 1 offer some protection to culturing embryos by preventing particles, such as dust, etc., from entering the slide and mixing with the culturing media while also allowing gaseous exchange necessary for embryo growth. To help reduce evaporation of the culturing media, the cover media (e.g., oil layer) is introduced to provide a film over the culturing media.

Using a cover media means an additional step is required in any process for culturing embryos in a slide. Not only is this time consuming, but it also requires additional tooling (i.e., a syringe/pipette suitable for delivering the cover media and different from the tooling delivering the culturing media) thus adding to the overall cost of the system and/or complexity of the preparation procedure. Moreover, depending upon the type of cover media, the cover media can also experience evaporation, although this is typically much slower than the evaporation of the water-based culturing media. Nevertheless, in some cases, the cover media can evaporate or show signs of evaporation over a period of weeks or, in extreme cases where the cover media is more volatile, a period of days.

The main purpose of the cover media is to reduce and virtually eliminate evaporation of the culturing media (predominately, if not entirely, of water from the water-based culturing media), which may otherwise cause changes in osmolality and osmotic stress to the embryos. The efficiency of the cover media in accomplishing this depends on the thickness of the layer and the permeability to water of the cover media, which together determine the evaporative loss. It is thus essential that adequate amounts of cover media are applied, and handling errors where too little cover media is applied have been known to compromise embryo development and treatment efficiency. Using too much cover media is expensive and may increase the likelihood of spills and contamination of the workspace. Most cover media are highly hydrophobic mineral oils that have been chosen because their low permeability to water constitutes efficient evaporation barriers. The cover media are normally checked by the manufacturer (and possibly by the clinics) to be non-toxic. However, toxic compounds such as volatile organic compounds (VOC's) may accumulate in the oil over time, and many cases have been reported where problems with slightly toxic mineral oil batches compromised embryo development and the overall efficacy of IVF treatments. Another potential problem as outlined above is the loose fitting lid in conventional culture dishes which does not prevent (or at least reduce) the likelihood and effects of spills and other types of mishandling (see above).

With this in mind, the inventors have conceived of new configurations of embryo slides and associated lids, for example for incubating embryos in an incubator, such as an incubator in an apparatus that provides for time-lapse imaging of embryos. Specifically, the inventors have devised a removable lid that comprises a gas permeable material and includes an engagement portion formed of a resilient material adapted to cooperatively engage with a side wall of the main body of the culture dish defining a reservoir region so as to compress a part of the engagement portion of the removable lid against the side wall to form a vapour-tight seal for the reservoir region, when the removable lid is coupled to the culture dish. The lid enables gaseous exchange between the environment enclosed by the lid and corresponding to the reservoir region (which includes a reservoir holding a quantity of culturing media and optionally embryos to be cultured and/or a quantity of other media such as water) and the environment external to the lid (which typically is the environment within an incubator apparatus holding the culture dish) as required for healthy embryo development and/or pH equilibration.

In addition, the lid is configured to resiliently engage with a side wall of the culture dish to form a vapour-tight seal for the reservoir region. The vapour-tight seal enables an enclosed volume to be formed between the lid and culture dish (i.e., a volume that includes the culturing media). The lid restricts the water vapour evaporated from the culturing media, as well as the liquid itself, from leaving the enclosed environment e.g., through the vapour-tight seal. Therefore, the vapour-tight seal provides the advantage of reducing the likelihood of spilling culturing media and/or contaminating the culturing media of other culture dishes.

Moreover, the lid acts to restrict or limit the amount of water vapour evaporated from the culturing media or other media included in the culture dish from permeating through the material of the lid itself. In this regard, the lid can be configured to control the amount of water vapour that leaves the enclosed space and subsequently can be configured to reduce this quantity to a tolerable amount for the particular application at hand. In some implementations, the permeability of the lid to water vapour is relatively lower than the permeability of the lid to gases (particularly $CO_2/O_2$). That is, in these implementations, the lid is more permeable to gas and restricts or prevents water vapour from escaping through the lid by virtue of having a lower permeability to water vapour. In other implementations, the lid may have a relatively higher or substantially equivalent permeability to water-vapour than gases. In these implementations, however, the permeability of the lid is selected to limit the total water vapour permeating through the lid (or more specifically, to limit the rate of permeability of water vapour). In this case, despite the lid having a higher permeability to water-vapour than gases, the volume of air enclosed by the lid can become saturated (or almost saturated) with water vapour because the rate at which water-vapour passes through the lid is limited/restricted, which subsequently reduces the amount of evaporation of the liquid media. In some implementations, this saturation may be achieved by providing a larger volume of water separately from a quantity of culturing media such that the saturation is predominantly provided by water vapour evaporated from the water. The permeability of the lid is not only dependent on the type of material the lid is formed from (i.e., the natural permeability of the material), but can also be dependent on the geometry of the lid itself (e.g., the thickness of the lid, the areal extent of the lid, etc.).

FIGS. 2 to 11 schematically represent a culture dish 22 and separate lid 60 according to certain embodiments of the invention. The culture dish 22 comprises a main body 24 which may be manufactured in accordance with any conventional techniques, for example injection moulding of a suitable plastics material. In particular, the culture dish 22 may be formed by injection moulding of a generally transparent polymer, for example a polystyrene, a polyester, such as PEN, PETg, and/or PET. The main body 24 may comprise a single moulding. As discussed further below, the culture dish 22 is coupled/joined to a lid 60 to provide an air-tight (and hence also a vapour-tight and water-tight) seal between the lid 60 and the main body of the culture dish (via an interference fit), wherein the lid 60 is separate and removable from the main body 24.

Before discussing particular features and aspects of the culture dish (slide/tray/carrier) 22 and lid 60 represented in FIGS. 2 to 11, an overall summary of the different figures is provided.

Figure 2:
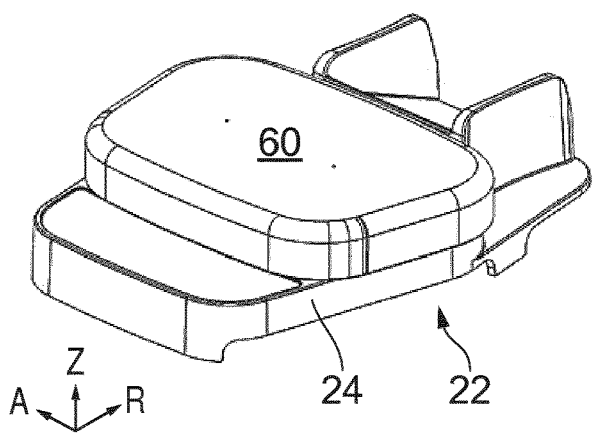
FIGS. 2 to 5 schematically represent different views of a culture dish having a separate lid attached thereto in accordance with an embodiment of the invention.

FIG. 2 schematically represents the culture dish 22, and in particular the main body 24 of the culture dish 22, and a separate lid 60 press-fit to the main body 24 to cover a reservoir 30 of the culture dish 22 in perspective view from above. This shows the main body 24 is generally sheet-like rather than solid, as is also apparent in some of the cross-sectional views discussed further below. The cross-sectional thickness of the material comprising the main body 24 may be generally around 1 or 2 mm, but may be thicker or thinner in different places according to the generally understood principles of construction for injection moulding of culture dishes.

Figure 3:
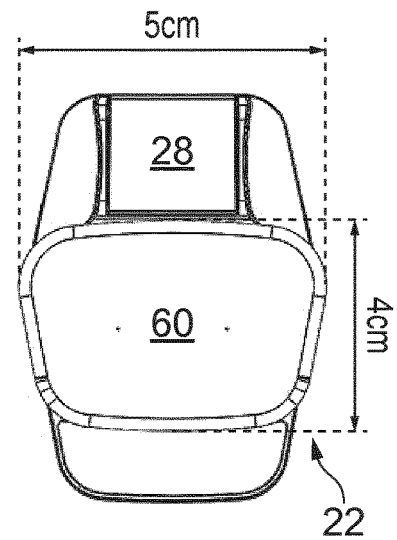

FIG. 3 schematically represents the culture dish 22 and lid 60 of FIG. 2 in perspective view from above.

Figure 4:
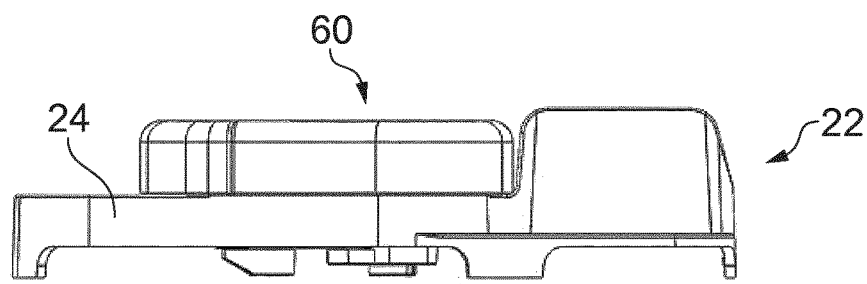

FIG. 4 schematically represents a side-on view of the culture dish 22 and lid 60 of FIGS. 2 and 3.

Figure 5:
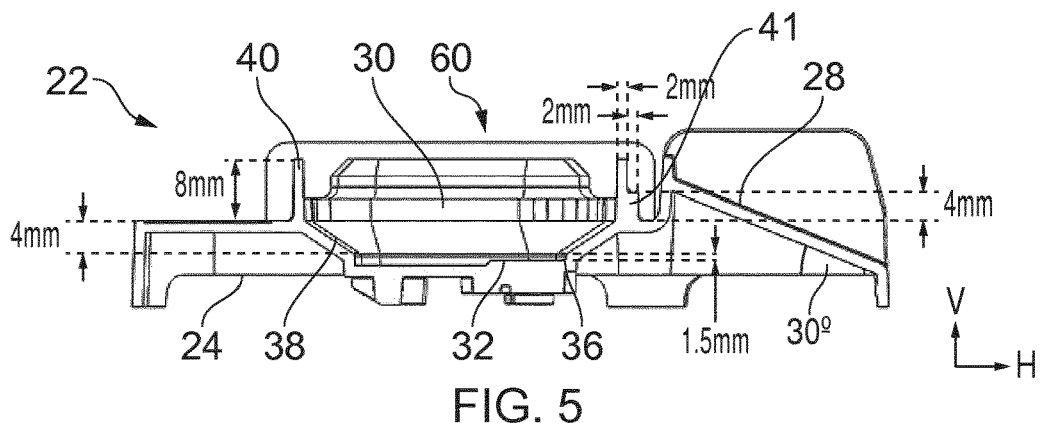

FIG. 5 schematically represents a cut-away side-on view of the culture dish 22 and lid for a cut running along that is horizontal and through the middle of the culture dish 22 and lid combination as represented in FIG. 4.

Figure 6:
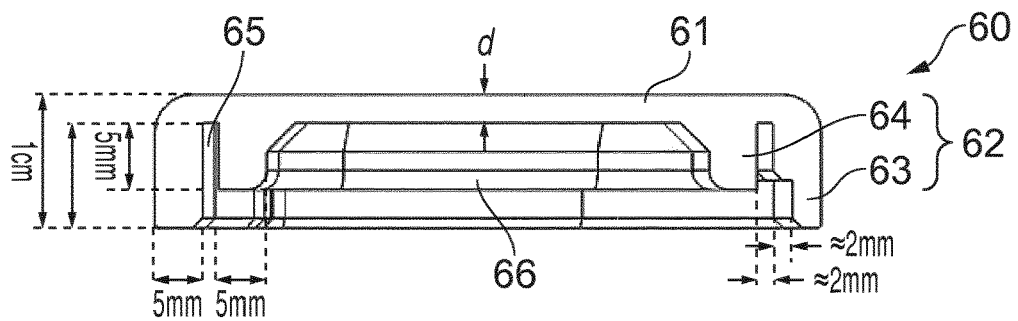
FIGS. 6 to 11 schematically represent different views of the lid of FIGS. 2 to 5 when the lid is not attached to the culture dish.

FIG. 6 schematically represents a cut-away side-on view of just the lid 60 of FIG. 5. The lid 60 has a main body portion 61 that is generally planar and has protruding side wall portions 62 extending away from the main body portion 61. The side wall portions 62 enable the lid 60 to abut and form an interference fit with the culture dish 22 to provide an air-tight seal between the lid 60 and the main body of the culture dish 22.

Figure 7:
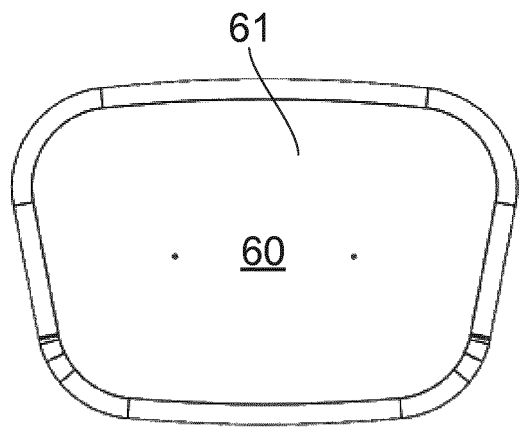

FIG. 7 schematically represents a perspective view from above of the outer surface of the lid 60.

Figure 8:
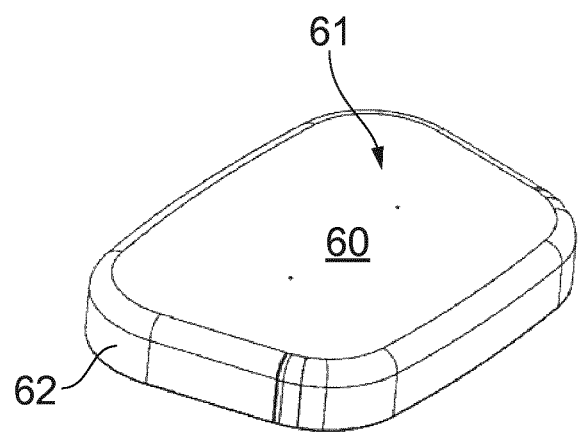

FIG. 8 schematically represents a perspective view of the lid 60 when viewed at an angle to both the horizontal and vertical planes.

Figure 9:

FIG. 9 schematically represents a side-on perspective view of the lid 60 of FIG. 7.

Figure 10:
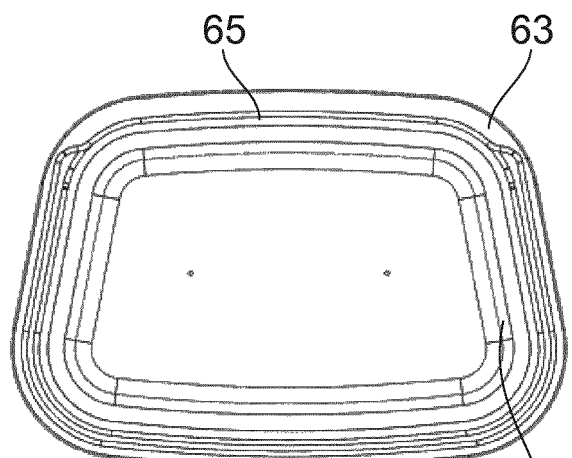
Figure 11:
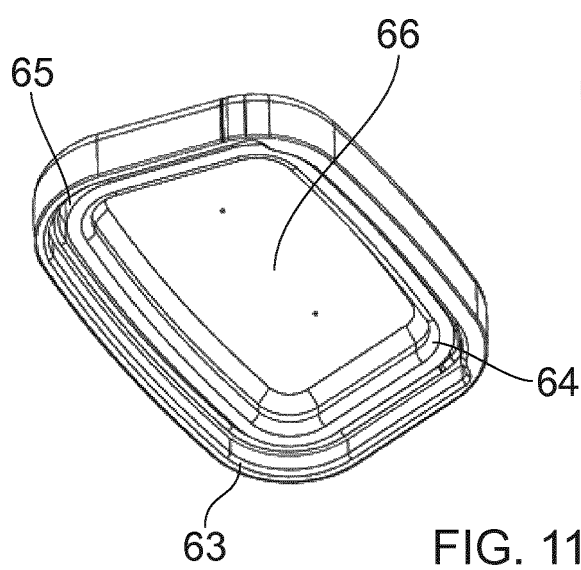

FIGS. 10 and 11 schematically represent perspective views of the lid 60 from below. The lid 60 has outer and inner wall portions 63, 64 that define a recess 65 for receiving a part of the culture dish 22. The outer and inner wall portions 63, 64 and the recess 65 are formed to continuously follow the perimeter of the main body portion 61 albeit spaced progressively apart from one another in an inward direction. The figures also show a cavity 66 formed in the lid 60.

Figure 12:
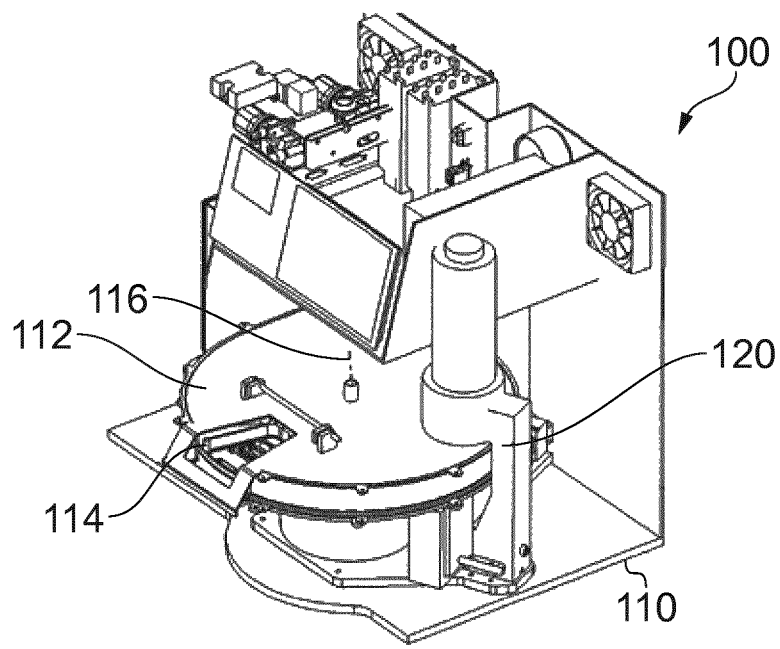
FIG. 12 schematically represents in perspective view an integrated apparatus for use in conjunction with the culture dish and lid represented in FIGS. 2 to 11.

The culture dish 22 and lid 60 represented in FIGS. 2 to 11 in this particular example are intended for use in an incubator apparatus 100 such as schematically represented in perspective view in FIG. 12. The incubator apparatus 100 represented in FIG. 12 may, for example, be of the kind described in WO 2015/113810 [4] and/or WO 2015/113809 [5]. However, it will be appreciated the specific incubator apparatus to be used for a culture dish including a lid according to embodiments of the invention (if indeed the culture dish is to be used for incubating embryos) is not overly significant.

Figure 13:
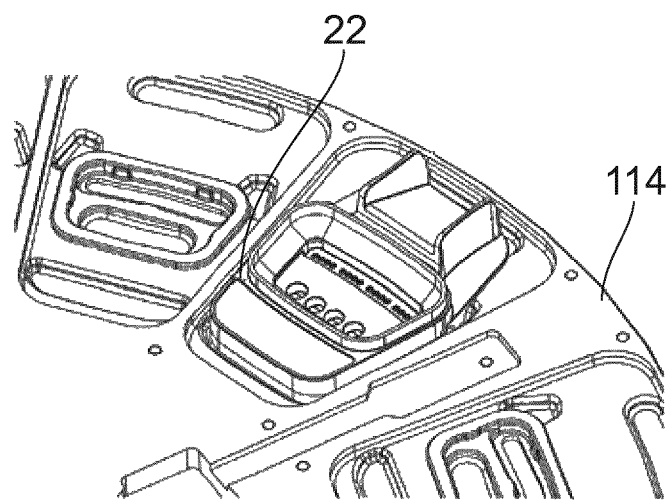
FIGS. 13 and 14 schematically represent different views of the culture dish and lid represented in FIGS. 2 to 11 in position in a slide carrier of the incubator apparatus represented in FIG. 12.
Figure 14:
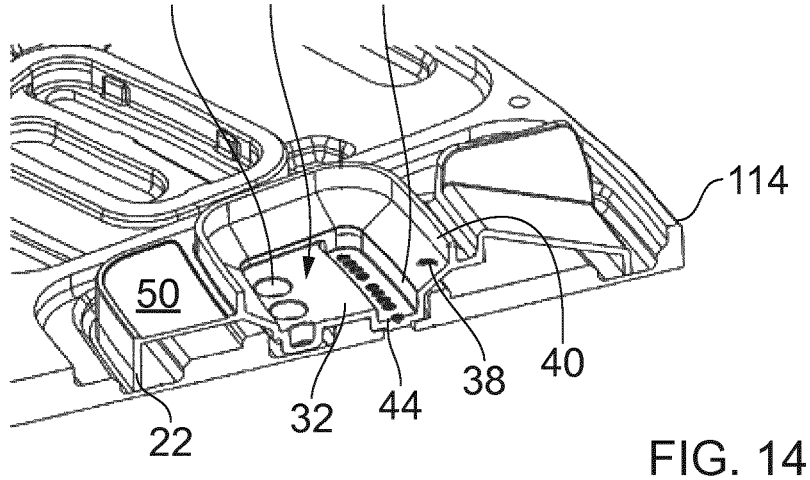

The incubator apparatus 100 in this example has a characteristic footprint on the order of 60 cm×50 cm and a height that is on the order of 50 cm. The apparatus 100 comprises an outer casing which is not shown in FIG. 12 so as to reveal various internal components of the incubator apparatus. The apparatus 100 comprises a base plate 110 to which various other components are mounted. At its heart the incubator 100 includes an incubation chamber defined by an incubation chamber housing 112 and a slide carrier 114. The slide carrier 114 comprises a plurality of compartments for holding respective embryo culture dishes of the kind represented in FIGS. 2 to 5 for holding embryos to be incubated within the incubation chamber. The slide carrier 114 is generally in the form of a circular disc, although only a small part of the slide carrier 114 is visible in FIG. 12. The slide carrier 114 is rotatable within the incubation chamber defined by the incubation chamber housing 112 about a rotation axis 116 to allow different culture dishes within the incubation chamber may be rotated into alignment with the imaging device for monitoring (image acquisition). A larger portion of the slide carrier 114 is shown in schematic perspective view in FIG. 13 without the surrounding incubator chamber housing 112 and with a culture dish 22 located in one of the slide carrier's compartments. FIG. 14 is similar to FIG. 13, but shows a partial perspective cut-away view through the culture dish 22 and slide carrier 114.

The incubator apparatus 100 further comprises an imaging device 120, in this case a digital microscope. The microscope 120 is mounted outside the incubation chamber in alignment with a viewing port in the incubation chamber housing 112 to allow the microscope to record images of embryos stored in culture dishes.

Overall, the operation and construction of the incubator apparatus 100 may follow known techniques, such as those described in WO 2015/113810 [4] and/or WO 2015/113809 [5].

Thus, in normal use, a culture dish 22 including a lid 60 according to an embodiment of the invention may be placed in a compartment of a slide carrier 114 of an incubator apparatus 100 of the kind represented in FIG. 12. The relative spatial arrangement of features of the culture dish 22 may be described with reference to its orientation during normal use.

Thus, the term horizontal may be used to describe a plane of the culture dish 22 as represented in FIG. 3, which in this example is generally the plane in which the culture dish 22 has its greatest areal extent. The term vertical may be used to describe a direction which is normal to the horizontal. Thus, the direction which may be referred to as a vertical direction for the culture dish is as schematically represented by direction arrow marked V in FIGS. 4 and 5. Directions referred to herein as horizontal directions for the culture dish are directions which are parallel to the plane of FIG. 3, for example as schematically represented by the direction arrows marked H in FIGS. 4 and 5. The vertical direction may also be referred to as the Z-direction for the culture dish 22. Because the culture dish 22 in this example is intended for use in an incubator in which culture dishes are rotated about an axis for sequentially aligning embryos with an imaging system, it can be convenient in some cases for directions in the horizontal plane of the culture dish 22 to be referred to within a circular coordinate system having its origin at the centre of rotation 116 of the slide carrier, a radial direction R extending away from the centre of rotation and an azimuthal direction A extending perpendicular to the radial direction. Thus the relative arrangement of features of the culture dish 22 may in some cases be described by reference to a radial direction R, an azimuthal direction A and a vertical direction Z, as schematically indicated in FIG. 2. The radial direction R may also be referred to as an axis of extent/length direction L for the culture dish. A width direction W for the culture dish may be defined as a direction which is horizontal and orthogonal to the length direction L. A height direction H for the culture dish may be defined as a direction which is vertical. Of course it will be appreciated these various directions are defined purely for the convenience in explaining the relative arrangement of some features of the culture dish and/or lid, and in particular having regard to an orientation of the culture dish and/or lid when in normal use and the terms are not intended to in themselves impose any particular structural limitations on the overall configuration of the culture dish 22 and/or lid 60 in an absolute sense.

Terminology such as "up" and "down" and "top" and "bottom" will be used herein having regard to the vertical direction for the slide and/or dish when in normal use. Thus the "top" of the culture dish and/or lid is the surface of the culture dish and/or lid which faces upwards when the culture dish and/or is in normal use, for example when containing embryos and media. The "bottom" of the culture dish and/or lid is the surface of the culture dish and/or lid which faces downwards when the culture dish and/or lid is in normal use. The edge surfaces of the main body of the culture dish which are generally orthogonal to its axis of extent may be referred to as the ends of the culture dish. The edge surfaces of the main body of the culture dish which are generally parallel to its axis of extent may be referred to as the sides of the culture dish.

As is apparent from the figures, the ends of the culture dish 22 in this example are generally straight while the sides are bent broadly around their middles so the sides taper inwards (see FIG. 3 in particular). This tapering allows multiple culture dishes to be conveniently arranged around a circle when placed in a slide carrier 114 of the kind represented in FIGS. 13 and 14. The bends in the sides of the culture dish and the outer corners between the ends and the sides are rounded. The culture dish 22 in this particular example has a characteristic length L of around 6.5 cm, a characteristic width W (at the widest point) of around 5 cm or so, and characteristic height H of around 1.5 cm. However, it will be appreciated that other sizes and shapes of culture dish may be selected according to the implementation at hand, for example to match the geometry of a holder for the culture dishes.

Referring to FIGS. 2 to 11, the culture dish 22 is suitable for holding one or more objects to be cultured, such as embryos, and comprises a main body 24, as discussed above. Alternatively it may contain media samples without objects to be cultured, which are placed in an incubator apparatus and allowed to equilibrate with the surrounding atmosphere. The equilibrated media sample may be used for subsequent culture or for further analysis such as pH measurements and other compositional analysis.

The main body 24 in the implementation shown comprises sixteen wells 42 for receiving embryos for culturing. In normal use an embryo culturing media, for example a water-based nutrient rich media, is also placed in the wells 42 with the embryos. In use, there will typically (although not always) be one embryo in each well 42 up to the number of embryos to be cultured.

The culture dish 22 comprises a reservoir 30 defined by a reservoir wall and a reservoir floor 32. The wells 42 are provided in the floor 32 of the reservoir 30. More particularly, in this example implementation the wells 42 are provided within a depression (trough) 44 provided in the reservoir floor 32, as best seen in FIGS. 5 and 14. The reservoir 30 is for holding a quantity of culturing media over the embryos when the culture dish is in use. In horizontal cross section the reservoir 30 has a generally quadrangular form with rounded corners. Accordingly, the reservoir wall comprises two sides running broadly parallel to the ends of the culture dish 22 and two sides running broadly parallel to the sides of the culture dish 22. Because the sides of the culture dish 22 are angled with respect to one another, the sections of the reservoir wall running broadly parallel to the sides of the culture dish 22 are also angled with respect to another.

The reservoir 30 in this example has a characteristic extent of around 3 cm between the sides running parallel to the ends of the culture dish 22 and a characteristic width between the sides running parallel to the sides of the culture dish of around 4 cm (at the widest point). The reservoir has a characteristic depth (from the top of the reservoir wall to the reservoir floor 32) of around 1.25 cm. However, it will be appreciated that other sizes and shapes of reservoir may be selected according to the implementation at hand, for example having regard to the intended use (e.g. a desired amount of culturing media to be used).

The reservoir wall extends upwardly from the reservoir floor 32 and in this example comprises three sections, each of which extends all around the reservoir 30. Thus, the reservoir wall comprises a vertical lower reservoir wall section 36 which meets the reservoir floor 32 and extends generally vertically upwards therefrom. Above the lower reservoir wall section 36 is a middle reservoir wall section 38. This extends upwardly from the lower reservoir wall section and is angled away from the vertical direction (i.e. inclined relative to the horizontal plane). Above the angled (middle) reservoir wall section 38 is an upper reservoir wall section 40. This extends generally vertically upwards from the top of the angled reservoir wall section 38 and generally defines a side wall of the reservoir.

In the particular example culture dish represented in FIGS. 2 to 11, and as schematically indicated in FIG. 5, the upper reservoir wall 40 has a height of around 8 mm and is formed to have step-like profile. In other words, the lower part of the upper reservoir wall includes a projection 41 that increases the width (in a horizontal direction) of the upper reservoir wall 40. The projection 41 has a height of around 4 mm and a width of around 2 mm. In this implementation, three sides of the upper reservoir wall 40 are provided with the projection 41. Specifically, the two sides of the upper reservoir wall 40 that are broadly parallel with the sides of the culture dish 22 and the longer of the two sides of the upper reservoir wall 40 that are broadly parallel with the ends of the culture dish 22. It will be appreciated the geometry of the reservoir may be different in different implementations.

The upper wall section 40 represented in FIGS. 5 and 14 extends above the level of the portion of the main body 24 of the culture dish 22 that surrounds the reservoir. Thus, the upper wall section 40 in effect provides a vertically extending side wall (or rim) around the reservoir. It should be appreciated, however, that in other implementations the side wall may be offset from the edge of the reservoir itself. However, the side wall nevertheless defines a reservoir region, which is a region of the culture dish that includes or incorporates the reservoir 30. The upper wall section 40 or side wall is configured to cooperatively engage with a corresponding engagement portion of the lid 60 to enable a resilient engagement of the lid 60 with the culture dish 22, specifically by compressing a part of the engagement portion of the lid 60 when the lid 60 is coupled to the culture dish 22, to provide a vapour-tight seal for the reservoir 30/reservoir region.

Turning now to the lid 60, FIGS. 6 to 11 schematically represent the overall geometry of the lid 60 in accordance with the described implementation. The geometry of the lid 60 may be selected to broadly match the size of the reservoir 30 in horizontal cross section. More specifically, the internal geometry of the lid 60 may broadly match the external extent of the upper wall section 40 in horizontal cross-section, and the height of the lid 60 may be selected to broadly correspond with the height of the upper wall section 40. At the very least, the internal geometry of the lid 60 is selected to provide an overlap between the lid and upper wall section 40 to create a vapour-tight fitting when the lid 60 is fitted to/engaged with the dish 22. Accordingly, the lid 60 can be readily located over the reservoir 30, as schematically represented in FIG. 5, such that the lid 60 covers the reservoir 30.

The lid 60 of this implementation comprises a main body portion 61 having a wall portion 62 extending from the peripheral edge of the main body portion 61. In FIG. 6, the main body portion 61 is substantially flat (i.e. planar) and is disposed extending in the horizontal plane while the wall portion 62 extends in the vertical direction with respect to the horizontal plane. However, the main body portion 61 may have a different vertical cross-section shape (e.g., curved) in other implementations. However, it will be appreciated that other dimensions may be selected according to the implementation at hand, for example having regard to the intended use (e.g. a desired equilibration time and/or amount of culturing media to be used). It should also be understood that the lid 60 in this implementation is separate from the dish 22 and so may be rotated or moved with respect to the reference frame defined above in relation to the culture dish 22. However, when the lid 60 is cooperatively engaged with the culture dish 22, the lid 60 and dish 22 can be considered to share the same reference frame. Accordingly, the same reference frame as described with respect to the culture dish 22 is used here to describe the features of the lid 60.

The shape of main body portion 61 is generally similar to the shape of the reservoir in this implementation. That is, in horizontal cross-section (see FIG. 7 or 10) the lid has a generally quadrangular form with rounded corners. The lid 60 comprises two sides that run broadly parallel to the ends of the culture dish 22 when fitted to the culture dish 22 and two sides that run broadly parallel with the sides of the culture dish 22 when fitted thereto. The sides running broadly parallel with the sides of the culture dish 22 are angled with respect to one another thereby generally following the shape of the sides of the culture dish 22 and upper reservoir wall 40. In this implementation, the lid 60 has a characteristic extent and a characteristic width slightly larger than the extent and width of the reservoir 30. By way of the example, the lid 60 has a characteristic extent of around 4 cm between the sides running parallel to the ends of the culture dish and a characteristic width of around 5 cm (at the widest point) between the sides running parallel to the sides of the culture dish 22.

The lid 60, and in particular the wall portion 62, which forms the engagement portion of the lid 60, is formed from a resilient material. In this implementation, the wall portion 62 includes an outer wall portion 63 and an inner wall portion 64. Both the inner wall portion 64 and the outer wall portion 63 project in a direction substantially orthogonal to the plane of the main body portion 61. In vertical cross-section (see FIG. 6) the corners between the main body portion 61 and the outer wall portion 63 are shown as being rounded, which may be advantageous in the removal of the lid 60 from a mould while also preventing any sharp edges on an outer surface of the lid 60 from arising (e.g., burrs or the like when manufacturing the lid 60). The characteristic extent of the outer wall portion 63 in the depth direction (vertically) is slightly larger than the characteristic extent of the upper reservoir wall 40. By way of example, the outer wall portion 63 has a characteristic extent of around 1 cm. The characteristic extent of the inner wall portion 64 in the depth direction (vertically) is less than the extent of the outer wall portion 63; for example, the characteristic extent may be around 5 mm.

The outer wall portion 63 extends substantially from the entire peripheral edge of the main body portion 61 of the lid 60. That is, the outer wall portion 63 follows a continuous pathway around the edges of the main body portion 61 when viewed in the horizontal plane (see FIG. 10). Therefore, the outer wall portion 63 defines the outer edges of the lid 60. In contrast, the inner wall portion 64 extends from a position within the peripheral edge of the main body portion 61 spaced from the outer wall portion 63 to form a recess 65. That is, the outer wall portion 63 surrounds the inner wall portion 64 separated by the recess 65, wherein the recess 65 also runs parallel to the inner and outer wall portions 64, 63.

The recess 65 is sized so as to receive the upper reservoir wall 40. As mentioned previously, three sides of the upper reservoir wall 40 include the projection 41 which increases the width of the upper reservoir wall 40 at the projection. The recess 65 is therefore provided with a characteristic extent that broadly corresponds to the different widths of the upper reservoir walls 40. With reference to FIG. 6, the recess 65 comprises an inner side and an outer side. The outer side is the side of the recess 65 that is formed by the outer wall portion 63, while the inner side is the side that is formed by the inner wall portion 64.

The recess in one side of the lid 60 corresponding to the shorter side of the lid 60 that runs parallel with the ends of the culture dish 22 when the lid 60 is fitted thereto has an outer side having a characteristic depth of 8 mm, and inner side having a characteristic depth of 5 mm, and a width of slightly less than 2 mm, e.g., 1.8 mm. The recess in the remaining three sides of the lid 60 has an outer side characteristic depth of 8 mm and an inner side having a characteristic depth of 5 mm. However, the width varies in a stepped manner in that the width of the recess 65 transitions from slightly less than 4 mm (e.g., 3.8 mm) to slightly less than 2 mm (e.g., 1.8 mm) at a position 4 mm from the lower edge of the outer wall portion 63 along the outer side of the recess 65. The presence of the projection 41 and stepped recess 65 may help to align and press the lid 60 onto the upper reservoir wall 40.

A function of the lid 60, and in particular the main body portion 61, is to cover the reservoir 30 (or more specifically the reservoir region defined by the upper reservoir wall 40). Accordingly, the lid 60 generally has a shape and characteristic extent to perform this function when placed over the reservoir opening. More specifically, the lid 60 is engaged with the upper reservoir wall 40 by pressing the outer and inner wall portions 63, 64 around/onto the upper reservoir wall 40 such that the upper reservoir wall 40 slots/fits into the recess 65. In this implementation, the characteristic width of the recess 65 is formed to be slightly less than the width of the upper wall portion 40. In this way, as the lid 60 is pressed onto the upper reservoir wall 40, the surfaces of the recess 65 (i.e., the inner wall portions 64 and outer wall portions 63, which form the engagement portion of the lid 60) are compressed by the outer reservoir wall 40 to form the vapour-tight seal. The lid is completely in place when the lower ends of the outer wall portion 63 abut the upper surface of the culture dish 22 and/or the horizontal part of the recess 65 abuts the upper edge of the upper wall portion 40.

It will be appreciated however that other shapes and/or sizes of lid 60 may be selected according to the implementation at hand. Equally, the various relationships between the outer and inner wall portions 63 and 64 can be varied; for example, the inner wall portion 64 may have the same characteristic depth as the outer wall portion 63. More generally, the lid 60 may be formed with dimensions (characteristic extents) that do not quite correspond to the characteristic extents of the upper reservoir wall 40 in order to provide the compression of the engagement portion when the lid 60 is cooperatively engaged with the upper reservoir wall 40.

In the described implementation, the lid 60 is formed from a single moulding of a resilient, gas permeable material (in particular to oxygen and/or carbon dioxide). That is, oxygen and carbon dioxide are able to permeate through the resilient material (with little resistance) and thus travel between the environment within the reservoir 30 and enclosed by the lid 60 and the environment outside the lid 60, thereby enabling gaseous exchange required by the culturing embryos. Direct gas consumption (i.e. oxygen) and production (i.e. carbon dioxide) by the developing embryos is largely immaterial to the relatively large amount of gases contained within the reservoir 30 and media contained within the culture dish 22. However, efficient and rapid gas exchange through the resilient membrane ensures timely equilibration of the gas and media composition within the culture dish 22 after placing the dish in an incubator. The lid 60 is normally attached to the culture dish 22 and closed outside the incubator thus entrapping a normal atmosphere of around 20% oxygen and 0.04% carbon dioxide in the reservoir 30/reservoir region. After placing the culture dish in an incubator with controlled gas composition (e.g. 5% oxygen and 6% carbon dioxide) it is desirable to equilibrate rapidly to ensure correct pH of the culturing media and reduced oxygen concentration for optimal embryo development, as described above. Substantial equilibration should take place within a few hours, preferably in less than 4 hours, more preferably less than 1 hour, most preferably in less than 30 minutes or even faster. Thus the resilient material constituting the lid has a relatively high permeability to carbon dioxide (e.g., allowing $CO_2$ to be transported through the lid 60 to the reservoir region enclosed by the lid 60) and if possible also to oxygen (though oxygen permeability is less critical as elevated oxygen is less detrimental to the developing embryo than pH stress, and embryo development is not severely restricted by prolonged exposure to oxygen).

However, excessive evaporation of the media may lead to osmotic stress to the embryo so the permeability of the resilient material to water vapour should be limited. Embryos are sensitive to osmotic stress and have been shown to prefer media with an osmolality of 255 to 295 mOsm/kg, and commercial media typically specify a more narrow range of osmolality e.g. 270+/−5 mOsm/kg. Nevertheless a limited evaporation during incubation is acceptable/tolerable and apparently does not interfere with embryo development or with the pH equilibrium. Preferably the evaporation should be less than 5% of the total media volume during the incubation time, more preferably less than 2% or most preferably 0.5% or even less. The material comprising the lid 60 and the material thickness, d, should thus be chosen to limit evaporative water loss to below 5% of the contained media, more preferably below 2%, for the required incubation time.

Therefore, the lid 60 is configured such that culturing media (and in particular water vapour generated by evaporation of the culturing media) is not able to readily permeate through the material of the lid 60 and is therefore restricted from the leaving the environment enclosed between the reservoir 30 and the lid 60. The lid 60 can be said to have limited permeability to water vapour evaporated from the culturing media, which means the permeability is chosen so as to limit the evaporative losses (or rather evaporative loss rate) of the quantity of culturing media.

The permeability of the lid 60 to both gases and water vapour evaporated from the liquid media is dependent upon a number of factors. Firstly, the material the lid 60 is formed from has certain permeability coefficients which are indicative of the material's natural permeability to the gas/vapour. The permeability coefficient, P, in equation 3 of Example 1 is a material specific coefficient which expresses the permeability properties of the material. The permeability coefficient is often conveniently expressed in the unit Barrer, where 1 Barrer=$10^{-10}$ $cm^3$ (STP)·cm/$cm^2$·s·cm-Hg. The permeability coefficient expresses the volume of gas/vapour (in $cm^3$ at STP), given a thickness of the material of 1 cm, and an area of 1 $cm^2$, which permeates through the material per second when under the pressure difference of 1 cm-Hg, which drives the gas/vapour across the material. In general, the higher the permeability coefficient (Barrer value), the lower the degree to which the material restricts gasses/liquids from passing through, i.e., the higher the overall gas/liquid transport through the material at a given pressure difference between inside and outside. Theoretical calculations of gas equilibration for a silicone lid based on literature values for permeability coefficients are presented in Example 1. Experimental data supporting the theoretical calculations for evaporative weight loss and pH equilibration is presented in Example 2 below.

The resilient material of the lid 60 may have a permeability coefficient selected from the group comprising: above 100 Barrer, above 500 Barrer, and above 3000 Barrer in terms of the relatively high permeability to gases (particularly carbon dioxide and also oxygen) and a permeability coefficient selected from the group comprising: below 100000, below 10000, and below 1000 in terms of the limited permeability to water vapour evaporated from the culturing media. In other implementations, the permeability coefficients may have a different value to those given because, as discussed below, the permeability coefficient is not the only factor that determines the overall permeability.

Permeability is also proportional to the area of the lid and inversely proportional to the thickness of the lid (Equation 3, Example 1). It is thus possible to reduce the required equilibration time by increasing the area, A, and/or reducing the thickness, d. The diffusive distance (i.e. thickness of the lid) is indicated by the double arrow marked d in FIG. 6. The optimal thickness depends on the permeability and desired pH equilibration time for a given application, as well as requirements for robustness when handling. The lid depicted in FIG. 6 has a thickness between 1 and 3 mm, which was also used for the theoretical calculations in Example 1 and the measurements described in Example 2 detailed later.

However, any dimensional changes will affect both the beneficial gas exchange of carbon dioxide and oxygen and the potentially detrimental evaporative loss of water vapour. While it may be possible to improve equilibration time by using a thin lid with a large surface area it could lead to excessive evaporation. As efficient and rapid equilibration of carbon dioxide is paramount to avoid pH stress after placing the culture dish in the incubator, the resilient material may have a larger than optimal permeability to water vapour. However, by enclosing a larger quantity of media within the reservoir region (e.g. 3 mL as in Example 1 and 2) it may still be possible to reduce the evaporative loss to less than 5% of the total media volume which causes negligible osmotic stress. The skilled person is able to configure the lid 60 in terms of material having a suitable permeability coefficient and/or overall geometry of the lid and/or the quantity of liquid media to be stored to obtain the desired degree of permeability of the lid 60. Depending on the implementation at hand, different amounts of media may be used, e.g., an amount of at least 0.5 mL, at least 1 mL, at least 2 mL, or at least 3 mL The lid 60 is constructed in accordance with the present disclosure to have a limited permeability to the vapour of the culturing media while allowing efficient gas exchange for carbon dioxide and oxygen. The lid 60 is designed to limit the amount of media (in vapour form) that can escape the enclosed environment compared to an open reservoir, yet provide efficient carbon dioxide permeability to facilitate pH equilibration. Limiting water evaporation ensures that there remains a sufficient quantity of culturing media in the reservoir for the duration of the culturing or equilibration process, and limit any osmotic stress due to increasing salinity following evaporation. The lid 60 is designed such that the limited permeability leads to a certain percentage or less of the contained volume of culture media in the culture dish escaping the reservoir per day. The certain percentages can be selected from the group comprising: 5% or less of the volume of culturing media; 4% or less of the volume of culturing media; 3% or less of the volume of culturing media; 2% or less of the volume of culturing media; 1% or less of the volume of culturing media; and 0.5% or less of the volume of culturing media. In other implementations, the certain percentage can be higher or lower than those given. These rates are measured in a dry environment (as generated by any suitable dry incubator apparatus) and at suitable physiological conditions, e.g., 37° C.

It should be understood that the actually quantity of culturing media (e.g., in grams) escaping the reservoir may be dependent upon the total amount of the culturing media present in the reservoir as well as the surface area of the media exposed to air. Moreover, it should also be understood that, due to evaporation and permeation though the lid 60, the volume of culturing media can change over the course of a day.

In order to meet the designed limit of e.g., 5% of the total volume of culturing media permeating through the lid per day, the corresponding lid (which will also have a large areal extent) will need to either be thicker or be formed of a material having a lower permeability coefficient than a lid and reservoir having a smaller areal extent. As should be appreciated, there is a trade-off between the certain design parameters. The skilled person will take into account these trade-offs when designing a lid and/or culture dish to form a suitable combination that provides the desired rate of permeability.

Accordingly, the lid 60 of the abovementioned implementations enables the degree of water vapour evaporated from the liquid media within the reservoir 30 permeating through the lid to be limited while achieving a high gas ($CO_2/O_2$) permeability for gaseous exchange. This is achieved by either providing a lid with an overall permeability to water vapour that is relatively lower than the permeability to gases, or by providing a lid that has a permeability to water vapour that enables the enclosed volume of air to become saturated with water vapour (which is also dependent upon the quantity of liquid media stored in the reservoir) to thereby reduce or limit the evaporative losses.

The lid 60 in the described implementation is a single moulding of resilient material and is formed using any suitable manufacturing technique. For example, in one implementation, the lid 60 is formed using an injection moulding process in which a liquid formulation of the resilient material is injected into a mould that is shaped in a way so as to form the lid, and the liquid formulation is subsequently hardened in the mould and removed. Forming the lid in a single moulding means that the manufacturing process is simplified (because there is no further moulding or attaching of other components). However, in other implementations, the lid may be formed of a plurality of components joined together to form the lid, such as the lid shown in FIG. 16 described in more detail below, which comprise resilient components 162, abutting reservoir wall 164, and rigid components 161, which may provide other benefits (e.g. transparency, different permeability coefficients or other desired properties).

The material used for the lid 60 may comprise an elastomer. Examples of such elastomers are natural rubber, poly(isoprene), neoprene, poly(chloroprene), poly(urethane), thermoplastic polyurethane, nitrile rubber, butyl rubber, poly(isobutene-coisonrene), poly(oxytetramethylene), poly(oxytetramethylene)glycol or any similar compound such as any of the elastomers mentioned in Example 3, or similar compounds with resilient properties. Elastomers with a high permeability to carbon dioxide are in some cases preferable as they will allow implementation of a lid with sufficient thickness to be sturdy and robust without compromising carbon dioxide equilibration time. In a further preferred implementation, the material used for the lid 60 consists of silicone such as polysiloxanes, dimethyl silicone, fluorosilicone, or poly(dimethylsiloxane). In another implementation the material used for the lid 60 may be a mixture based predominantly on silicon and including one or more further materials. While the water vapour permeability of silicone is quite high (e.g. 36000 Barrer), it is matched by a substantial permeability to carbon dioxide, (e.g. 3250 Barrer) and to oxygen (e.g. 600 Barrer). Silicone is thus applicable as a resilient lid material and forms the basis for the calculations in Example 1 as well as the actual measurements in Example 2 using the lid design described in FIG. 5 to FIG. 11). To limit water evaporation to an acceptable/tolerable level (i.e. <5% per day) the total media volume is larger (at 3 mL) than what is normally used for incubations with an oil cover (recommended at 0.4 mL).

In other implementations, the material of the lid 60 comprises Teflon AF (or a mixture thereof), a family of amorphous fluoropolymers based on copolymers of 2,2-bistrifluoromethyl-4,5-difluoro-1,3-dioxole (PDD). The Teflon AF could be engineered to be a resilient elastomer or alternatively it could be a transparent, gas permeable, rigid insert in the lid (e.g. component 161 in FIG. 16). A particular advantage of Teflon AF is the unusually high permeability for carbon dioxide at 2800 to 3900 Barrer, with very low water permeability at 1170 to 4100 Barrer. Other materials that can be used for the lid 60 and provide the same functionality for the lid may also be used in accordance with the principles of the present disclosure.

The resilient material in some implementations is transparent in order to enable the imaging of the embryos or other objects to be cultured stored within the reservoir without removal of the lid 60. One intended use of the culture dishes 22 is for culturing one or more embryos, by placing the embryos/dishes 22 in an incubator apparatus 100 including a rotating slide carrier 114. Typically, the culturing embryos are imaged using a microscope 120 during the culturing process. Therefore, it is convenient for the lid 60 to remain in place while the imaging 120 is being performed, thereby avoiding the additional step of removing the lid before imaging.

In other situations, the lid 60 may be used to protect the culturing media samples from evaporation during equilibration with the environment inside an incubator, such as the incubator 100 described with reference to FIGS. 12 to 14, prior to performing pH measurements and the like. This can be to test the levels of carbon dioxide within the incubator to ensure that the environment is not too acidic or to alkaline for embryos to be cultured. A sample of culturing media is placed in the dish 22, the lid 60 is placed over the dish enclosing the culturing media, and then the culturing media sample is inserted into an incubator and left for a period of time. Gaseous exchange occurs through the lid 60 as described above which affects the pH level of the culturing media. After the predetermined amount of time (e.g., 8 hours, 24 hours, or 72 hours, etc.) the sample is removed and the pH level tested (e.g., by inserting a syringe through the lid to extract the culturing media or by removing the lid and testing the sample directly). The lid 60 when used for pH measurements may therefore be opaque or coloured to prevent transmission of light and protect the reservoir 30 from incident light. A coloured non-transparent lid may also prevent any unapproved use for cultivation of embryos in non-sterile pH validation dishes. However, it should be understood that a transparent lid 60 will also be able to be used during equilibration prior to pH measurement and the like.

As shown in FIGS. 6 and 11, the lid 60 is provided with a cavity 66 defined by the inner wall portion 64. The cavity 66 can take any shape but is broadly positioned so as to overlie the reservoir 30 when the lid 60 is press fit to the culture dish 22. In the implementation described, the cavity generally follows the same shape as the inner wall portion 64 and therefore has two sides that are broadly parallel with the ends of the culture dish 22 when the lid is attached to the culture dish 22 in normal use, and two sides that are broadly parallel with the sides of the culture dish 22 (and angled in a similar manner with respect to one another) when attached to the culture dish 22 in moral use. The characteristic depth of the cavity 66 is around 5 mm (i.e., the height of the inner wall portion 64). As a result, the cavity 66 reduces the thickness, d, of the main body 61 of the lid 60, specifically in the region directly above the reservoir 30, and can therefore be sized to influence the permeability values as described above. More generally, the cavity 66 is a region of the lid that is relatively thinner than the other regions of the lid. The permeability of the lid can therefore be customised/controlled by placing of the cavity within the main body of the lid 60. Although only one cavity is shown, multiple cavities can be provided. The walls separating a plurality of cavities can act as ribs to provide structural support to the lid. As seen in FIG. 6, the cavity 66 has a surface defined by the inner surface of the inner wall portion 64 and, in this implementation, the inner surface of the wall portion has a curved section followed by an inclined section. The specific shape of the inner surface of the inner wall 64 is not significant for the principles of the present disclosure. In this case, however, the shape may be chosen so as improve the releasability from the mould for forming the lid 60 and/or to improve the structural integrity of the lid 60. Additionally, the presence of the cavity 66 helps to improve the flexibility of the lid 60 which can be advantageous when attaching the lid 60 to the culture dish 22.

Although not shown, the lid 60 may be further provided with an upwardly extending lip 62 around its perimeter in other implementations. This may naturally help prevent users from moving their fingers across the surface of the lid 60 when handling the lid 62 and/or main body 24 of the culture dish 22. This can be especially advantageous if the culture dish with transparent lid 60 is intended for use in an incubator apparatus having time-lapse imaging functionality. This is because the imaging systems in this type of incubator apparatus will generally rely on optical paths that pass through the lid 60 (e.g. for imaging or illumination), and so it can be important to reduce scattering and or shadowing that might occur from fingerprints or other marks on the lid 60.

As described above, the removable lid 60 is separate from the culture dish 22 and can be attached to, and removed from, the culture dish 22. To help remove the lid 60 from the culture dish, the outer wall portions 63 may be provided with some form of non-smooth outer surface—for example, a surface having knurling or some raised sections forming a pattern. This enables a user to firmly grip the outer surfaces of the wall portion 62 and apply a force (substantially in the direction away from the culture dish) in order to remove the lid 60. Generally, the interference fit will be configured to apply a compressive force great enough to prevent liquid and/or vapour from escaping from the reservoir by travelling along the surfaces of the outer wall portion 63, but low enough that a user can slide/remove the lid 60 with relative ease.

Thus, and as described above, there are various aspects of culture dishes and lids provided in accordance with embodiments of the invention which helped to improve on existing designs. It will be appreciated that culture dishes and lids in accordance with various embodiments of the invention may incorporate some or all of the above-identified features, either alone or in various combinations. Furthermore, in accordance with certain embodiments of the invention, a culture dish may comprise additional features and/or variations of the features described above.

The lid 60 described above may be provided with any suitable dimensions or in any suitable shape to couple with or join to a corresponding culture dish. That is, the principles of the present disclosure are not limited to the specific culture dish shown in FIGS. 2 to 11. For instance, in some embodiments, the lid may be shaped so as to cover the main body 4 of the culture dish/slide 2 in FIG. 1 in a manner as generally described above. Such a possible embodiment is shown in FIGS. 17 to 19, which describe a lid design compatible with the culture dish shown in FIG. 1. FIGS. 17 to 19 schematically represent a similar lid 60' designed to fit the culture dish 2 shown in FIG. 1. In FIGS. 17 to 19, similar features to the lid 60 shown in FIGS. 2 to 11 are indicated with similar reference signs, differing only by the presence of a ' (prime). The primed version of the feature is substantially similar, in terms of material used and function, to the non-primed version and a detailed description will be omitted here. Instead the skilled person is referred back to the corresponding description of the non-primed version above. The main differences of lid 60' reside in the shape of the lid as described now.

FIG. 17 schematically represents a perspective view from above of a generally rectangular lid 60', which fits the culture dish 2 shown in FIG. 1. The lid 60' comprises two longer parallel sides separated by two shorter parallel sides provided orthogonally to the longer sides. The lid 60' also comprises a side wall portion 62' extending downwardly from a generally planar main body portion of the lid. FIG. 18 schematically represents a perspective view of the lid 60' from below while FIG. 19 schematically shows a cross sectional view of the lid 60' of FIGS. 17 and 18. The lid 60' has outer and inner wall portions 63', 64' that define a recess 65' for cooperatively engaging with a side wall of the culture dish 2 shown in FIG. 1 (the side wall defining the reservoir region of dish 2, e.g., the part of the main body 4 excluding the recess 12). The outer and inner wall portions 63', 64' and the recess 65' are formed to continuously follow the perimeter of the main body of the culture dish to provide a vapour-tight seal when the lid 60' is engaged with the culture dish 2. The recess 65' is substantially greater than the recess 65 so as to fit the shape of the culture dish 2 (i.e., to mate with the thicker side wall of the main body portion 4 of culture dish 2). The inner wall portion 64' is configured to engage with recess 12 in the main body portion 4 of culture dish 2, while the outer wall portion 63' is configured to engage with the outer surface of the main body portion 4. Again, the side wall causes the inner and outer wall portions 64', 63' to compress when the lid is coupled to the dish 2. The figure also shows a cavity 66' formed in the lid 60'. It should be appreciated that lid 60' is one example configuration of a lid that can be constructed to engage with slide 2; the skilled person will appreciate that alternative designs can be employed for the same function—for example, inner wall 64' may be omitted in some implementations.

In other implementations, the lid may be sized to engage with a petri-dish shaped culture dish (e.g., a similar shaped dish to that shown in FIGS. 15 and 16 described below). It should be appreciated by one skilled in the art that regardless of the shape of the slide 2, 22, a corresponding lid 60 being permeable to gas and configured to form a vapour-tight seal can be formed in order to provide a vapour-tight seal with the given slide.

Moreover, the lid 60 above has generally been described such that it has a greater extent than the upper reservoir wall 40 in the horizontal plane. However, the present disclosure is not limited to lids such as this. For example, in other implementations, the lid 60 has a characteristic extent in the horizontal plane that is substantially equal to the extent of the opening defined by the upper reservoir wall 40. In this case, the outer surface of the outer wall portion 63 is configured to abut (and optionally apply a compressive force to) the inner surfaces of the upper reservoir wall 40. That is, the lid 60 is configured to fit inside the upper reservoir wall 40 such that, when the lid 60 is press fit to the culture dish 22, the upper reservoir wall 40 surrounds the outer perimeter of the lid 60. In these implementations, the upper reservoir wall 40 compresses the outer wall portion 63 of the lid (generally in a direction towards the centre of the lid).

In other implementations, the inner wall portion 64 is not included in the lid 60. In these implementations, the interference fit is provided only by the outer wall portion 64 abutting the upper reservoir wall 40. The abutment may either be realised by the inner surface of the outer wall portion 63 abutting the outer surface of the upper reservoir wall 40 or by the outer surface of the outer wall portion 63 abutting the inner surface of the upper reservoir wall 40.

As has already been explained, it will of course be appreciated the various example dimensions and geometric configurations described above may be modified in accordance with other embodiments of the invention. For example, the overall shape and size of a culture dish may be selected in accordance with an incubator apparatus in which the culture dish is to be stored. It will also be appreciated that whereas the above-described embodiments have focused on application of culturing dishes for incubating embryos, culturing dishes in accordance with other embodiments of the invention may be used for culturing other objects, or for equilibrating media samples under culture conditions.

It will furthermore be appreciated that culture dishes according to other embodiments of the invention may incorporate some or all of the features of the culture dish 22 described above without some of the other features of the culture dish 22 described above. That is to say, it will be appreciated that various features of embodiments of the invention described above are independently beneficial and can be used separately from other ones of the various features of embodiments of the invention described above. In accordance with some embodiments of the invention, a culture dish may be provided having a well with a design incorporating a shelf section to help prevent particles from sinking to the bottom of the well and/or non-circular cross-section. In broad summary, it will be appreciated that embodiments of the invention may comprise any appropriate combinations of the features described above, and in particular features which are functionality independent of one another may be incorporated together or separately in different embodiments.

Figure 15:
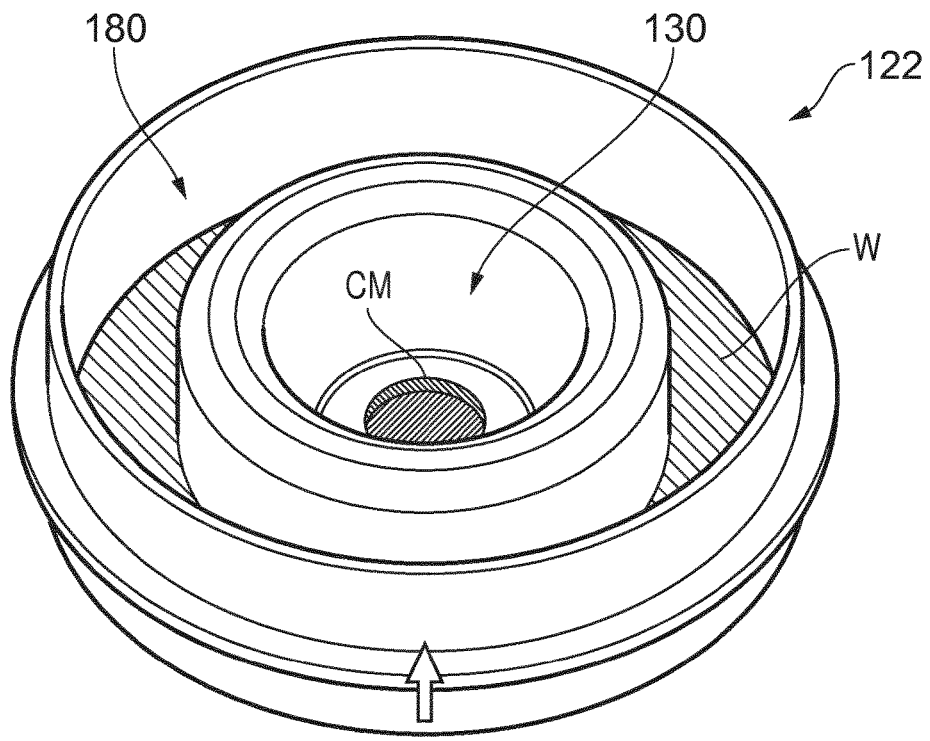
FIGS. 15 and 16 schematically represent an alternative culture dish including a second reservoir for holding a quantity of other media, such as water.
Figure 16:
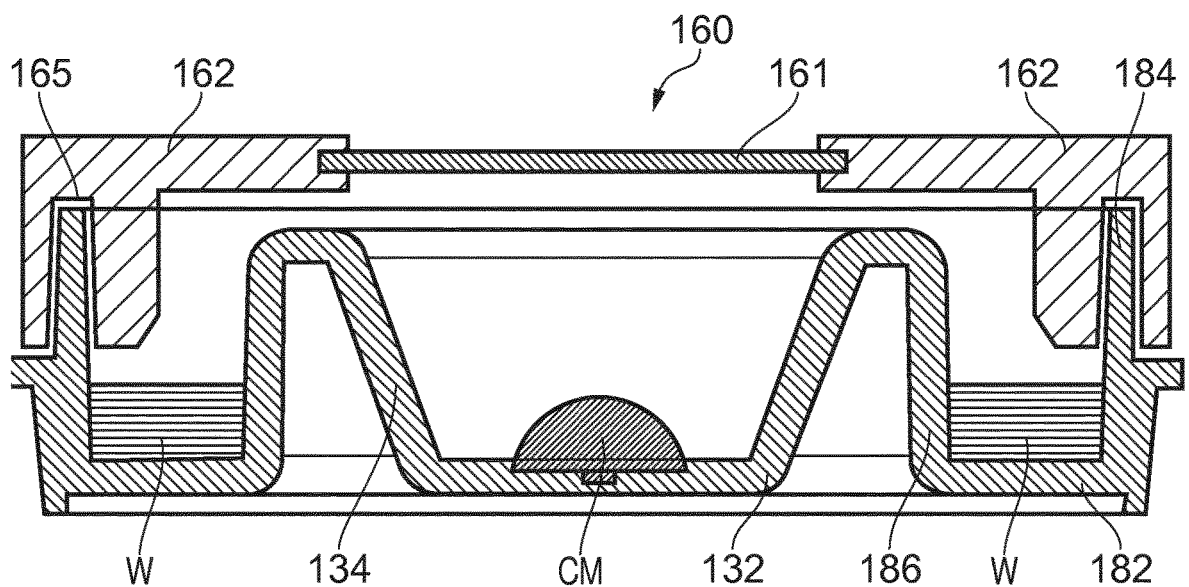

FIG. 15 schematically shows a perspective view of a culture dish 122 comprising a second reservoir 180 filled with a quantity of water W and separated from a first reservoir 130 containing culturing media according to other implementations, while FIG. 16 schematically shows a cross-sectional view of the culture dish 122 and associated lid 160.

The culture dish 122 of this implementation comprises a first reservoir 130 which includes a reservoir floor 132 and a reservoir wall 134 extending approximately perpendicularly to the reservoir floor 132 (at an angle of about 80°) and a second reservoir 180 which is U-shaped in cross-section and comprises a reservoir floor 182 and a vertically extending inner and outer walls 186 and 184 respectively. The first and second reservoirs 130, 180 are provided within a common reservoir region defined by the outer wall 184. The culture dish 122 is approximately cylindrical in shape and has a corresponding circular cross-section when viewed from above. By way of example only, the outer diameter of the culture dish 122 is approximately 6 cm and it has a characteristic extent in the height direction of approximately 1.5 cm. The culture dish 122 is formed from any of the materials that can be used for dish 22, e.g., polystyrene.

The first reservoir 130 is provided at the centre of the culture dish 122 while the second reservoir 180 surrounds the outer sides of the first reservoir 130—in other words, when viewed from above, the second reservoir 180 forms an annulus surrounding the first reservoir 130 and concentric therewith. The diameter of the first reservoir 130 at its greatest point is, in this example, approximately 3 cm. The reservoir floor 132 and the reservoir wall 134 extending approximately vertically from the floor 132 define the volume of the first reservoir 130. This volume is sized to receive a quantity of culturing media; in FIGS. 15 and 16 this is shown as a droplet of culturing media CM placed an approximately the centre of the first reservoir 130, although any suitable amount of culturing media may be placed in the first reservoir 130. In this implementation, the characteristics height of the first reservoir is slightly less than the height of the dish 122, e.g., approximately 1.4 cm.

The culturing media CM may or may not contain one or more embryos depending on whether the dish and lid are to be used for pH equilibration or culturing the one or more embryos. Although not shown in FIG. 15 or 16, the dish 122 may be provided with one or more wells for receiving individual embryos and a quantity of culturing media within the individual wells and over the embryos. In cases where the pH level of media stored in an incubator apparatus over a period of time is to be tested, the wells may be omitted.

The second reservoir 180 has an inner diameter corresponding to the outer diameter of the first reservoir, and an outer diameter corresponding to the outer diameter of the dish 122. In this regard, for ease of discussion, the second reservoir 180 is connected to the outer reservoir wall 134 of the first reservoir through inner wall 186. As seen in FIG. 16, inner wall 186 extends vertically towards/from the second reservoir floor 182 and is joined to the upper edge of the first reservoir wall 134. The outer wall 184 of the second reservoir 180 is spaced from the inner wall 186 by a constant amount and is connected thereto through the reservoir floor 182. In effect, the second reservoir 180 defines a region for holding liquid that is different from the volume for holding liquid of the first reservoir 130, thereby allowing the culturing media in the first reservoir to be kept substantially separate from the second reservoir 180.

As seen in FIG. 16, a lid 160 is provided that engages with the dish 122 in a manner similar to lid 60. Lid 160 is formed from two main parts; a main body 161 and a side wall portion 162. The main body 161 is formed in a disk shape and is formed from a suitable material; in this case a rigid polymer, which may be transparent and/or have desirable permeability properties. An example of an optically transparent rigid polymer suitable for main body 161 is polystyrene. In contrast, the side wall portion is formed in an annular shape when viewed from above and is arranged to receive the disk shaped main body between the inner edges of the annular shape. The side wall portion 162 is formed from any suitable resilient material, e.g., an elastomer or rubber. The side wall portion 162 may be formed with a circular recess concentric with the annular side wall portion 162 and extending radially from the inner edge of the side wall portion 162 to enable the main body 161 to be stably and tightly held between the inner edges of the side wall portion 162. The outer parts of the side wall portion 162, as viewed in FIG. 16, are formed to have an inverted U-shaped portion defining a recess 165, the recess 165 being sized to receive the outer wall 184 of the second reservoir 180. In other words, the U-shaped portions of the side wall portion 162 are configured to cooperatively engage with the outer wall 184 (side wall of the culture dish 122) in a similar manner to how the side wall portion 62 is configured to cooperatively engage with outer reservoir wall 40 of the implementation described in FIGS. 2 to 11 to provide a vapour-tight seal for the reservoir region when the lid 160 is coupled to the dish 122. The elastomeric material is compressed by the outer wall 184, as the recess 165 is sized to have a width slightly less than the width of the outer wall 184.

As mentioned, the lid 160 may be formed from two main parts, which may be formed of different materials. In FIG. 16, the main body 161 is formed of a polystyrene, which may also be transparent to enable imaging of the first reservoir 130 and any embryos contained therein. In contrast, the side wall portion 162 is formed from any material that has the properties of a relatively high permeability to gases and a limited permeability to vapour evaporated from the culture media. This may include any of the materials discussed with regards to lid 60. The main body 161 does not have to have the same permeability properties. In other implementations, however, it is the main body 161 that is formed from a material having a relatively high permeability to gases and a limited permeability to vapour evaporated from the culture media, (e.g. Teflon AF) while the side wall portion may or may not also be formed from a material having these properties.

In a similar manner to lid 60, lid 160 provides suitable gaseous exchange (particularly to oxygen and carbon dioxide) between the environment enclosed by the lid 160 and dish 122 and the external environment. Equally, owing to the vapour-tight seal provided by side wall portions 162, lid 160 also prevents or substantially reduces spillages of the culturing media, thereby avoiding wastage and reducing the chance of cross-contamination as described with regards to lid 60. In other words, lid 160 is a further example of a lid that is suitable for omitting the cover media from a reservoir containing culturing media because lid 160 provides a relatively high permeability to gases and a vapour-tight seal for the reservoir region.

As mentioned above, there are a number of different factors that can determine how the lid 160 is designed to obtain a certain relatively high permeability to gas while limiting the amount of water vapour evaporated from the culturing media. A contributing factor, which will reduce media evaporation, is the additional humidity provided by water evaporation from the second reservoir 180. The second reservoir 180 is provided in dish 122 in order to receive a quantity of other media or water W. The water may have a quantity of $CO_2$ stored/dissolved therein which can be released into the reservoir region to help expedite pH equilibrium. Evaporation of both the water W and culturing media CM will occur, but the humidity of the environment enclosed by the lid 160 and dish 122 is provided by both the amount of evaporated water W and the (water) vapour evaporated from the culturing media CM. The relative contribution of W and CM will be proportional to their respective surface areas, if they both have the same temperature and similar salinity (i.e. similar water activity). As the proposed design features a much larger surface area for the water, W, in the reservoir 180, as opposed to the area of the media droplet, CM, the evaporation of the culture media will be reduced substantially. In other words, by enclosing a second reservoir 180 containing a volume of water W by a lid 160 having low permeability to water vapour, the evaporation of the culturing media can be slowed.

Water or distilled water is comparatively inexpensive compared to culture media and is thus a suitable other media to use. However, the skilled person will be aware of alternative other media that may also increase the humidity of the environment trapped between the lid 160 and reservoirs 130, 180. Because the evaporation rate of a body of water is at least partly dependent on the surface area of the body of water, the geometry of the dish 122 and second reservoir 180 in particular can be chosen/configured to provide a certain evaporation rate of the water W.

It should also be understood that, although the second reservoir is shown with regards to a petri-dish shaped dish 122, a second reservoir 180 can be implemented in any shaped dish. For example, a second reservoir 180 may be used in dish 22, e.g., located in the reservoir floor 32 of dish 22. The second reservoir 180 may not be annular in shape but may alternatively have any cross-sectional shape when viewed from above, such as a square/rectangle.

The lid 160 above is formed from two parts (main body 161 and side wall portion 162) which are joined in a manner that provides an air-tight seal, wherein each of the main body 161 and side wall portion may be formed of different materials having different permeability properties. However, in a similar manner to lid 60, lid 160 in some implementations is formed from a single moulding of the same resilient material (that is, the main body 161 and side wall portion 162 are integrally formed from the same material).

In summary, in accordance with the implementation of FIGS. 15 and 16, there is provided an apparatus comprising a culture dish and lid, wherein the culture dish includes a main body that comprises a first reservoir for receiving a quantity of culturing media and a second reservoir separate from the first reservoir and for receiving a quantity of other media (such as water), wherein the lid comprises an engagement part that is configured to engage with a side wall of the culture dish defining a reservoir region, wherein the engagement portion is configured to cooperatively engage with the side wall of the main body of the culture dish so as to compress a part of the engagement portion to form a vapour-tight seal for the reservoir region.

Thus, disclosed is an apparatus comprising a culture dish and a removable lid, wherein the culture dish comprises a main body having a side wall defining a reservoir region for receiving a quantity of liquid media, and the removable lid is arranged to cover the reservoir region during normal use, wherein the lid comprises a gas permeable material and includes an engagement portion formed of a resilient material adapted to cooperatively engage with the side wall of the main body of the culture dish so as to compress a part of the engagement portion of the removable lid against the side wall to form a vapour-tight seal for the reservoir region when the removable lid is coupled to the culture dish. The lid fitted to the culture dish enables a substantial portion of the culturing media to remain in the environment enclosed between the reservoir and the lid without use of a cover media while allowing gaseous exchange for embryo growth or pH equilibration to occur, without excessive evaporation which could cause osmotic stress and/or change equilibrium pH.

Further particular and preferred aspects of the present invention are set out in the accompanying independent and dependent claims. It will be appreciated that features of the dependent claims may be combined with features of the independent claims in combinations other than those explicitly set out in the claims.

Example 1: Simulated Gas Exchange Through Silicone Lid

Example 1 shows a simulation of the equilibration rate for $CO_2$ through a silicone membrane (as an example of the material suitable for use as the lid 60, 60' or 160) and the concurrent evaporative loss of water. This was performed using Fick's first law of diffusion:

$$J = -D^*(\partial \varphi / \partial x) \quad \text{(Equation 1)}$$

Where J is the diffusive flux of which express the amount of substance that will flow through a unit area during a unit time interval.

D is the diffusion coefficient.

$\varphi$ is the concentration i.e. amount of substance per unit volume.

x is the coordinate along the diffusion axis.

For the following simulation we will estimate the integrated flux as:

$$F = J^*A \quad \text{(Equation 2)}$$

Where F is the total flux through the silicone lid and A is the area of the lid.

For diffusive flux of gasses through a membrane it is normal practice to use the partial pressure of the gas at either side of the membrane as concentration, and the diffusion coefficient expressed as a permeability coefficient in Barrer. Using this conventional nomenclature we get:

$$F = -A^*P^*(p2-p1)/d \quad \text{(Equation 3)}$$

Where F is the total flux through the membrane. [Unit: cm3/s]

A is the area of the lid [Unit: cm2]

P is the permeability coefficient. [Unit: Barrer=$10^{-1}*cm^3$ (STP)$*cm*cm^{-2}*s^{-1}*cm\text{-}Hg^{-1}$]

p2 is the gas concentration outside membrane: [Unit: cm-Hg]

p1 is the gas concentration inside the membrane: [Unit: cm-Hg]

d is the thickness of the membrane [Unit: cm]

A specific implementation of the lid depicted in FIGS. 2 to 11, as used in the following calculation, has the following properties:

Area: A=12.57 cm$^2$
Thickness: d=1.5 mm=0.15 cm
Enclosed volume between lid and culture dish: V=9.53 cm$^3$
Media filling of slide: V-media=3 mL=3 cm$^3$
Remaining air volume: V-air=V−V-media=6.53 cm$^3$
Permeability coefficient for carbon dioxide: 3250 Barrer=$3250*10^{-10}*cm^3*cm*cm^{-2}*s^{-1}*cm\text{-}Hg^{-1}$
Permeability coefficient for water vapour: 36000 Barrer=$36000*10^{-10}*cm^3*cm*cm^{-2}*s^{-1}*cm\text{-}Hg^{-1}$ It is assumed that the gas within the reservoir 30 of FIG. 3 is saturated with water vapour at the onset of the simulation (i.e. a humidity of 100%) and remains at 100% through media evaporation. The humidity outside the enclosure is assumed to be 0%. The difference in water vapour concentration across the lid is thus constant with an inside concentration of:

p1=6.20% of gas volume at 37° C.=4.71 cm-Hg (constant)
p2=0% of gas volume at 37° C.=0 cm-Hg (constant)
The total amount of liquid media within the slide is 3 mL which corresponds to 4230 cm$^3$ water vapour at 37° C.

Carbon dioxide outside the enclosure is 6% at the onset of the simulation and 0% inside.

p1=0% of gas volume at 37° C.=0 cm-Hg, initially but gradually increasing
p2=6% of gas volume at 37° C.=4.56 cm-Hg (constant)

As carbon dioxide permeates the lid and enters the reservoir 30 it will dissolve in the media and be dissolved as carbonic acid in equilibrium with bicarbonate. We can use the Henderson-Hasselbach equation to calculate the bicarbonate concentration in equilibrium with an ultimate carbon dioxide concentration of 6%:

$$pH = 6.1 + Log([HCO^{3-}]/(0.03*pCO^2)) \quad \text{(Equation 4)}$$

If the equilibrium pH is 7.3 we get:

$$[HCO^3] = (0.03*pCO^2)*10^{\wedge}(pH-6.1) = 21.7 \text{ mmol/L}$$

At equilibrium we thus have a total $CO_2$ content within the slide of 2.04 cm$^3$, of which 1.65 cm$^3$ is dissolved as bicarbonate.

We can now use the formula for the flux calculation and our values for total water content (i.e. 4230 cm$^3$) and equilibrium $CO_2$ content (2.04 cm$^3$) to simulate: a) $CO_2$ equilibration and b) water evaporation within the media sample contained in the culture dish 22 from FIGS. 2 to 5 covered by the example silicone lid 60 shown in FIGS. 2 to 11.

Figure 20:
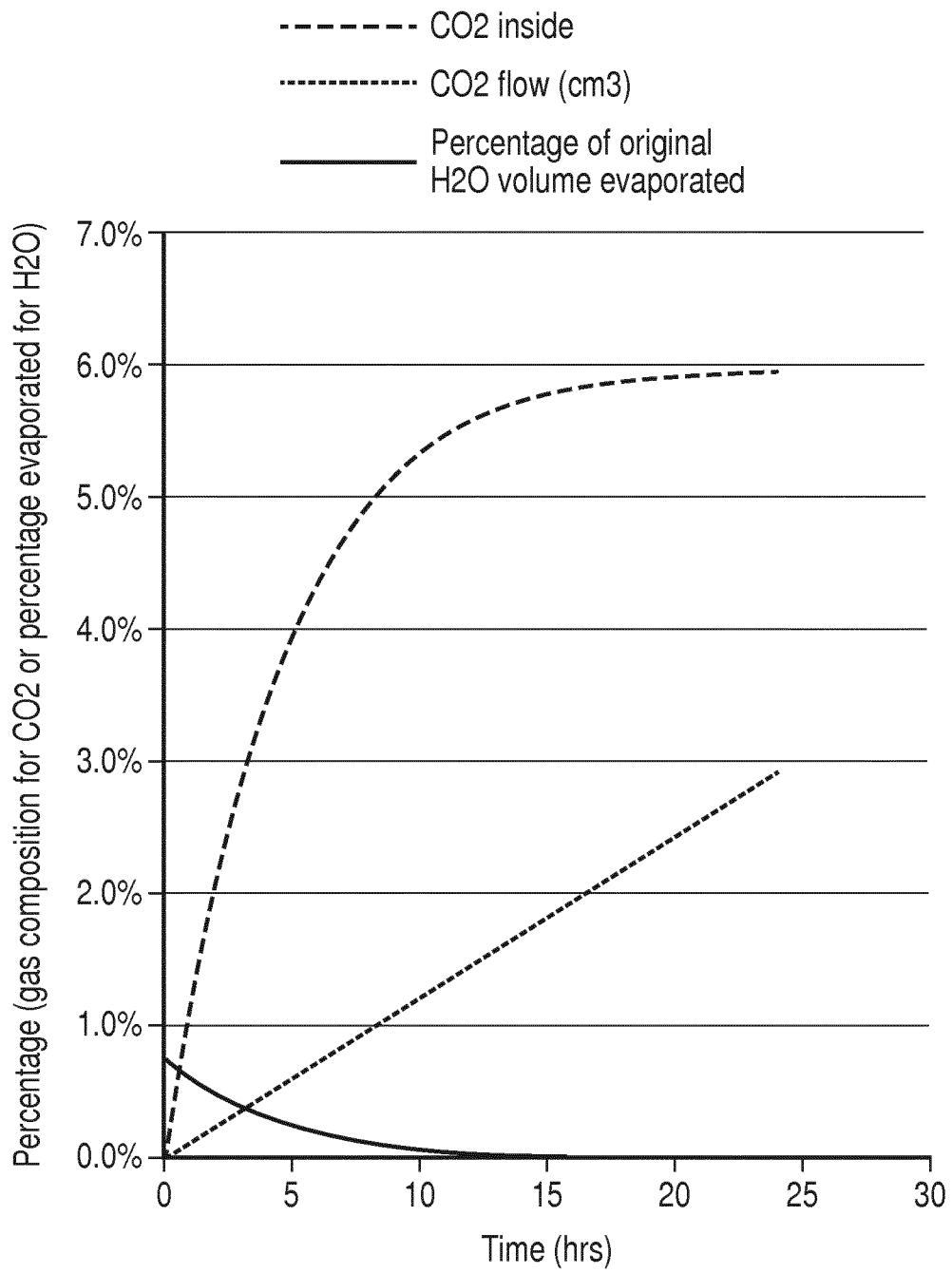
FIG. 20 is a graph showing simulated gas exchange, carbon dioxide equilibration, and evaporation in culture dish covered by a resilient lid, as explained in Example 1.

FIG. 20 is a graph showing the simulated changes in $CO_2$ concentration for the media contained in the culture dish, and the percentage of media which is likely to be lost due to evaporation (y-axis) against time (x-axis). The $CO_2$ concentration increases sharply and reaches 5% after about 8 Hrs. It is thus to be expected that pH equilibration is largely complete after 8 hours according to the simulation.

Water loss due to evaporation is linear as we assume the humidity outside the culture slide is kept constant at 0% relative humidity. The calculated water loss after 24 hours is about 3% of the initial 3 mL media (i.e. about 90 μL). As ambient air rarely is completely devoid of water vapour, and p2 is more likely 10 to 30% relative humidity it is expected that the actual evaporative loss will be somewhat smaller.

Example 2: Measured pH Equilibration and Evaporation

Example 2 provides an experimental evaluation of the theoretical calculations in Example 1. This was performed by incubating a 3 mL un-equilibrated media sample in a polystyrene culture dish (EmbryoSlide+, Vitrolife A/S, Denmark) covered with an example silicone lid, e.g., as shown in FIGS. 2 to 11. The example silicone lid was injection moulded from the silicone type QWF-50 (AVK gummi, Låsby, Denmark) according to the dimensions shown on the FIGS. 2 to 11.

The silicone lid covered EmbryoSlide+ culture dishes with 3 mL G-TL media (Vitrolife A/S, Denmark) were incubated in the EmbryoScope+ incubator (Vitrolife A/S, Denmark) at 37° C. in 6% carbon dioxide and 5% oxygen. pH was measured in media samples using an iSTAT (Abbott, USA), and the evaporative loss was measured by weight changes using a XB 320M high precision weight (Precisa, Switzerland). An empty EmbryoSlide+ with silicone lid was used as a control to verify reproducibility of weighings.

Figure 21:
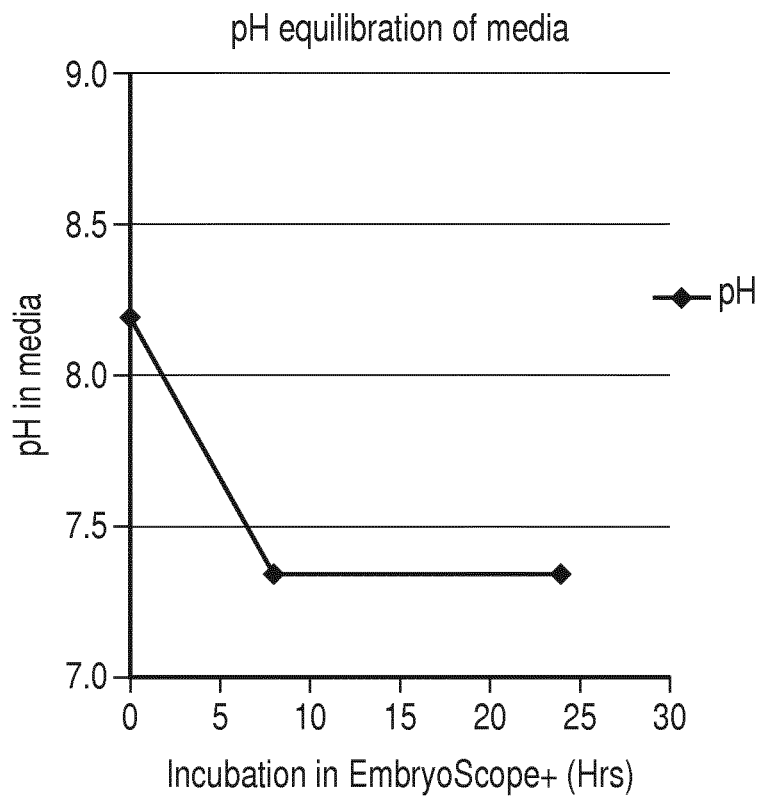
FIG. 21 and FIG. 22 are graphs showing measured pH equilibration, and evaporative weight loss in culture dish covered by a resilient lid respectively, as explained in Example 2.

FIG. 21 is a graph showing the pH level in the media (y-axis) as a function of incubation time (x-axis). The initial pH in the non-equilibrated media was approximately 8.2. After 8 Hrs the pH was substantially equilibrated to a value of 7.362, which remained constant at 7.357 after 24 Hrs.

Figure 22:
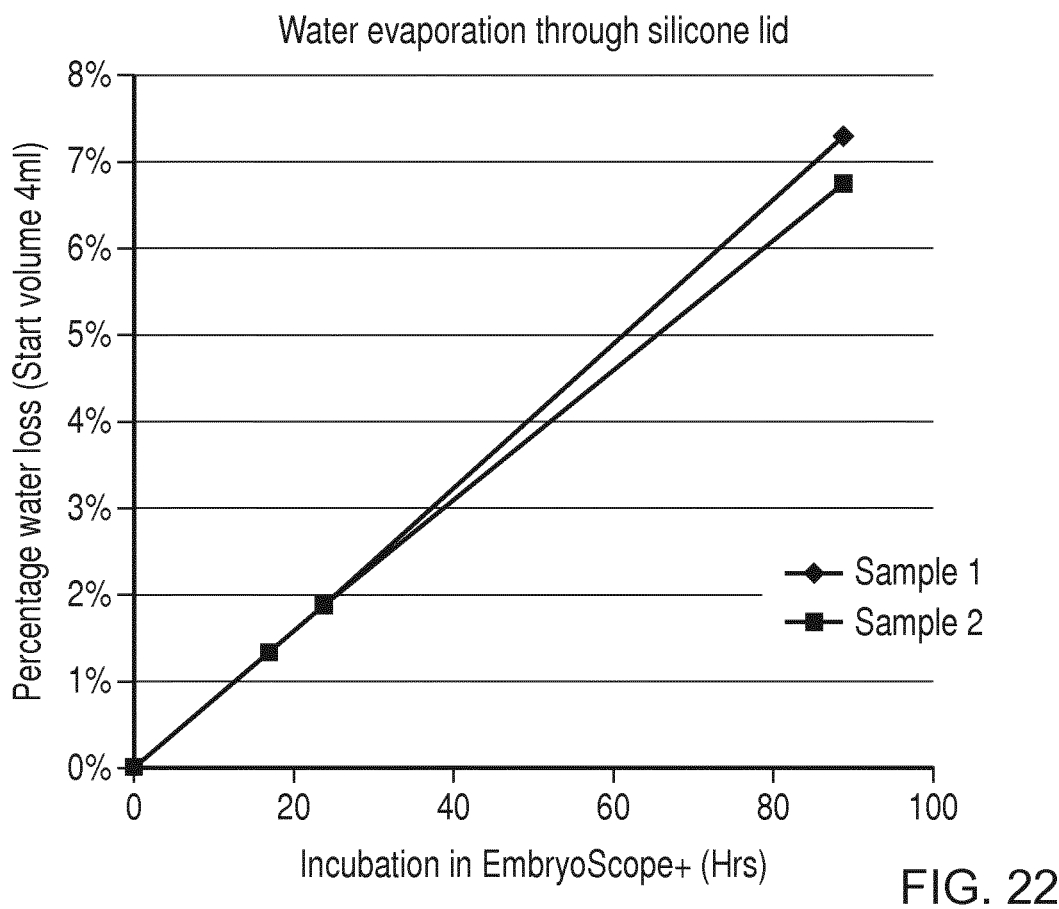

FIG. 22 is a graph showing the percentage of evaporated water loss (y-axis) as a function of incubation time (x-axis). The graph shows a linear evaporative water loss over a four-day period. The daily loss of media amounted to about 2% thus slightly lower than the expected evaporation, but remained constant throughout the period.

We thus conclude a remarkable agreement between the theoretically estimated changes and the actual observed values. As the pH was well equilibrated after about 8 hours and remained relatively constant for 24 hours during which time only about 2% of the media volume were lost to evaporation we conclude that the media sample within would be suitable for determination of equilibrium pH for the given media at the given $CO_2$ incubation concentration.

The EmbryoSlide+ containing the media sample covered by the described silicone lid would thus be a valuable tool to determine the ultimate pH for a given media sample incubated in an incubator with the given gas composition.

Example 3: Elastomers

Example 3 provides a non-comprehensive listing of example elastomers that may be suitable for use in lids 60, 60', 160. Note that although the permeability coefficients to CO2/O2 and water vapour may be different, the geometry of the lid (and in particular the thickness) can be configured to provide a lid having the desired transport properties for CO2/O2 and water vapour (i.e. a relatively high gas transport and a relatively low water vapour transport through the lid). The examples elastomers are:

Acrylonitrile-butadiene copolymer.
Brominated isobutylene-isoprene copolymers
Butadiene-acrylonitrile-ethylene glycoldimethacrylate copolymers
Butadiene-acrylonitrile-methacrylic acid copolymer.
Butadiene-styrene-methacrylic acid copolymer.
Chloroprene polymers.
Chlorotrifluoroethylene-vinylidene fluoride copolymer.
Ethylene-propylene copolymer elastomers which may contain polymer units derived from 5-methylene-2-norbornene and/or 5-ethylidine-2-norbornene.
Ethylene-propylene-dicyclopentadiene copolymer.
Ethylene-propylene-1,4-hexadiene copolymers containing polymer units derived from 1,4-hexadiene.
Hydrogenated butadiene/acrylonitrile copolymers (CAS Reg. No. 88254-10-8) produced when acrylonitrile/butadiene copolymers are modified by hydrogenation of the olefinic unsaturation
Isobutylene-isoprene copolymer.
Polyamide/polyether block copolymers prepared by reacting a copolymer of omega-laurolactam and adipic acid with poly(tetramethylene ether glycol).
Polybutadiene.
Polyester elastomers derived from the reaction of dimethyl terephthalate, 1,4-butanediol, and a-hydro-omegahydroxypoly(oxytetramethylene).
Polyisoprene.
Polyurethane resins derived from the reaction of diphenylmethane diisocyanate with 1,4-butanediol and polytetramethylene ether glycol.
Polyurethane resins derived from reactions of diphenylmethane diisocyanate with adipic acid and 1,4-butanediol.
Rubber, natural.
Silicone basic polymer
Silicone (Si) elastomers containing methyl groups.
Silicone (Psi) elastomers containing methyl and phenyl groups.
Silicone (Vsi) elastomers containing methyl and vinyl groups.
Silicone (Fsi) elastomers containing methyl and fluorine groups.
Silicone (PVsi) elastomers containing phenyl, methyl, and vinyl groups.
Styrene-butadiene copolymer.
Vinylidene fluoride-hexafluoropropylene copolymers
Vinylidene fluoride-hexafluoropropylenetetrafluoroethylene copolymers

REFERENCES

[1] WO 09/003487 (Unisense Fertilitech A/S)
[2] WO 01/002539 (The Danish Institute of Agricultural Sciences)
[3] WO 2015/169499 (Unisense Fertilitech A/S)
[4] WO 2015/113810 (Unisense Fertilitech A/S)
[5] WO 2015/113809 (Unisense Fertilitech A/S)

What is claimed is:

1. An apparatus comprising a culture dish and a removable lid, wherein the culture dish comprises a main body having a side wall defining a reservoir region for receiving a quantity of liquid media, and the removable lid is arranged to cover the reservoir region during normal use,
wherein the lid includes an engagement portion formed of a resilient material adapted to cooperatively engage with the side wall of the main body of the culture dish so as to compress a part of the engagement portion of the removable lid against the side wall to form a vapour-tight seal for the reservoir region when the removable lid is coupled to the culture dish, wherein the lid is a resilient, gas-permeable material and comprises a main body portion and a side wall portion, wherein the side wall portion is configured to resiliently engage with the side wall of the main body of the culture dish to form the vapour-tight seal.

2. The apparatus of claim 1, wherein the lid is permeable to carbon dioxide and/or oxygen.

3. The apparatus of claim 2, wherein the lid has a permeability coefficient to carbon dioxide and/or oxygen selected from the group comprising: above 100 Barrer, above 500 Barrer, or above 3000 Barrer.

4. The apparatus of claim 1, wherein the lid has a permeability coefficient to water vapour evaporated from the quantity of media selected from the group comprising: below 100000 Barrer, below 10000 Barrer, or below 1000 Barrer.

5. The apparatus of claim 1, wherein the lid is constructed such that, in use, less than 5% of the media volume per day, preferably less than 2% of the media volume per day, or more preferably less than 0.5% of the media volume per day is able to permeate through the lid when the apparatus is placed in a dry environment at physiological temperatures.

6. The apparatus of claim 1, wherein the lid encloses a volume of air between the lid and the reservoir of the main body portion of the culture dish, and wherein the lid has a permeability to water vapour evaporated from the liquid media that enables the enclosed volume of air to become saturated with water vapour.

7. The apparatus of claim 6, wherein the permeability of the lid to water vapour is chosen based on at least one of: the volume of liquid media to be stored in the reservoir, the exposed surface area of the quantity of liquid media when stored in the reservoir, the shape of the reservoir, and the shape of the portion of the main body the engagement portion is configured to resiliently engage with.

8. The apparatus of claim 1, wherein the reservoir is configured to hold a total quantity of media above 0.5 mL, preferably above 1 mL, more preferably above 2 mL, and even more preferably above 3 mL.

9. The apparatus of claim 1, wherein the quantity of liquid media comprises a quantity of culturing media and a separate quantity of liquid comprising water, and wherein the reservoir region comprises a first reservoir for holding the quantity of culturing media and a second reservoir for holding the separate quantity of liquid comprising water.

10. The apparatus of claim 1, wherein the resilient material comprises an elastomer.

11. The apparatus of claim 1, wherein the lid comprises at least one region having a reduced thickness such that the permeability to gas at the at least one region is higher than the permeability to gas other than at the at least one region.

12. The apparatus of claim 1, wherein the engagement portion of the lid comprises an outer side wall portion provided adjacent the peripheral edge of the lid and an inner side wall portion surrounded by the outer side wall portion and separated from the outer side wall portion by a recess, wherein, when the lid is engaged with the side wall of the culture dish, the outer side wall portion is configured to abut a first side of side wall of the culture dish while the inner side wall portion is configured to abut a second, opposite side of the side wall of the culture dish.

13. The apparatus of claim 1, wherein the lid includes a surface configured to act as a gripping portion for a user to grip the lid and remove the lid from the culture dish.

14. The apparatus of claim 1, wherein the lid is transparent to enable imaging of the contents of the reservoir when the lid is engaged with the main body.

15. The apparatus of claim 1, wherein the lid is opaque to prevent exposure of the contents of the reservoir to light when the lid is engaged with the main body.

16. The apparatus of claim 1, wherein the lid is formed by injection moulding.

17. A removable lid for use with a culture dish, the culture dish having a main body comprising side wall defining a reservoir region for receiving a quantity of liquid media, wherein the removable lid is arranged to cover the reservoir region during normal use,
wherein the lid comprises a gas permeable material and includes an engagement portion formed of a resilient material adapted to cooperatively engage with the side wall of the main body of the culture dish so as to compress a part of the engagement portion of the removable lid against the side wall to form a vapour-tight seal for the reservoir region when the removable lid is coupled to the culture dish.

18. A mould for forming the lid according to claim 17.

19. A method of culturing at least one object, the method comprising:
providing a culture dish having a side wall defining a reservoir region;
placing one or more objects to be cultured and a quantity of liquid media within the reservoir region of the culture dish;
applying a removable lid to cover the reservoir region, wherein the removable lid comprises a gas permeable material and includes an engagement portion formed of a resilient material adapted to cooperatively engage with the side wall of the main body of the culture dish so as to compress a part of the engagement portion of the removable lid against the side wall to form a vapour-tight seal for the reservoir region when the removable lid is coupled to the culture dish; and
allowing the one or more objects to culture.

20. A method of determining culture conditions such as pH within a culture dish, the method including:
providing a culture dish having a side wall defining a reservoir region;
placing a quantity of liquid media within the reservoir region of the culture dish;
applying a removable lid to cover the reservoir, wherein the removable lid comprises a gas permeable material and includes an engagement portion formed of a resilient material adapted to cooperatively engage with the side wall of the main body of the culture dish so as to compress a part of the engagement portion of the removable lid against the side wall to form a vapour-tight seal for the reservoir region when the removable lid is coupled to the culture dish;
placing the culture dish in an incubating apparatus and allowing the dish to equilibrate with the environment within the incubating apparatus; and
performing measurements such as pH measurements on the liquid media within the reservoir region after equilibration.

21. The method of claim 19, wherein the method does not comprise adding a quantity of oil to the reservoir region after adding the liquid media and before applying the removable lid to the culture dish.

22. The apparatus of claim 1, wherein the resilient material comprises silicone.

* * * * *